US012637689B2

(12) United States Patent
Kim et al.

(10) Patent No.: US 12,637,689 B2
(45) Date of Patent: May 26, 2026

(54) mRNA CONSTRUCT FOR PROTEIN EXPRESSION AND USE OF SAME

(71) Applicant: KOREA RESEARCH INSTITUTE OF BIOSCIENCE AND BIOTECHNOLOGY, Daejeon (KR)

(72) Inventors: Tae Don Kim, Daejeon (KR); Hee Young Kang, Daejeon (KR); In Pyo Choi, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 992 days.

(21) Appl. No.: 17/825,800

(22) Filed: May 26, 2022

(65) Prior Publication Data

US 2022/0290176 A1     Sep. 15, 2022

Related U.S. Application Data

(63) Continuation-in-part of application No. PCT/KR2020/016988, filed on Nov. 26, 2020.

(30) Foreign Application Priority Data

Nov. 26, 2019    (KR) ........................ 10-2019-0152938

(51) Int. Cl.
*C12N 15/85*        (2006.01)
*A61K 40/15*        (2025.01)
(Continued)

(52) U.S. Cl.
CPC .............. *C12N 15/85* (2013.01); *A61K 40/15* (2025.01); *A61K 40/31* (2025.01);
(Continued)

(58) Field of Classification Search
CPC ...... C12N 15/85; C12N 15/62; C12N 5/0646; C12N 2510/00; C12N 2840/203;
(Continued)

(56) References Cited

U.S. PATENT DOCUMENTS

| 5,807,707 A | 9/1998 | Andrews et al. |
| 5,824,497 A | 10/1998 | Andrews et al. |
| | (Continued) | |

FOREIGN PATENT DOCUMENTS

| CN | 107868791 A | 4/2018 |
| CN | 109097396 A | 12/2018 |
| | (Continued) | |

OTHER PUBLICATIONS

Bochkov, Y.A., and A.C. Palmenberg (2006) Translational efficiency of EMCV IRES in bicistronic vectors is dependent upon IRES sequence and gene location BioTechniques 41(3); 283-292 (Year: 2006).*

(Continued)

*Primary Examiner* — Scarlett Y Goon
*Assistant Examiner* — Audrey L Buttice
(74) *Attorney, Agent, or Firm* — Hauptman Ham, LLP

(57)        ABSTRACT
The present invention relates to an mRNA construct, comprising a target protein or peptide coding region and an IRES region downstream of the target protein or peptide coding region, wherein the mRNA construct of the present invention can stably maintain the expression of a target protein for a long time while being stably present in the cell.

12 Claims, 21 Drawing Sheets
Specification includes a Sequence Listing.

(51) Int. Cl.

| | |
|---|---|
| *A61K 40/31* | (2025.01) |
| *A61K 40/40* | (2025.01) |
| *A61K 40/42* | (2025.01) |
| *C07K 14/705* | (2006.01) |
| *C07K 14/725* | (2006.01) |
| *C07K 14/805* | (2006.01) |
| *C12N 5/0783* | (2010.01) |

(52) U.S. Cl.

CPC ........ *A61K 40/4254* (2025.01); *A61K 40/429* (2025.01); *C07K 14/7051* (2013.01); *C07K 14/70521* (2013.01); *C07K 14/805* (2013.01); *C12N 5/0646* (2013.01); *A61K 2239/31* (2023.05); *A61K 2239/38* (2023.05); *A61K 2239/49* (2023.05); *A61K 2239/55* (2023.05); *C07K 2319/02* (2013.01); *C12N 2510/00* (2013.01); *C12N 2840/203* (2013.01)

(58) Field of Classification Search

CPC .......... C12N 2501/515; C12N 2501/65; C12N 2501/51; C12N 2830/50; A61K 40/15; A61K 40/31; A61K 40/4254; A61K 40/429; A61K 2239/31; A61K 2239/38; A61K 2239/49; A61K 2239/55; A61K 39/0013; A61K 48/005; A61K 35/17; C07K 14/7051; C07K 14/70521; C07K 14/805; C07K 14/705; C07K 2319/02; C07K 2317/622; C07K 16/2803; A61P 35/00

See application file for complete search history.

(56)                  References Cited

U.S. PATENT DOCUMENTS

| | | | |
|---|---|---|---|
| 7,157,272 | B2 | 1/2007 | Daly |
| 9,994,858 | B2 | 6/2018 | Daly |
| 11,352,638 | B2 | 6/2022 | Plank et al. |
| 2004/0043468 | A1* | 3/2004 | Mauro ............... C12N 15/1034 435/325 |
| 2004/0063186 | A1* | 4/2004 | McGrew ................ C12N 15/67 435/325 |
| 2004/0115704 | A1 | 6/2004 | Daly |
| 2004/0209274 | A2 | 10/2004 | Daly |
| 2005/0003482 | A1 | 1/2005 | Fang et al. |
| 2005/0042721 | A1 | 2/2005 | Fang et al. |
| 2007/0298417 | A1 | 12/2007 | Daly |
| 2008/0280356 | A1 | 11/2008 | Fang et al. |
| 2010/0317096 | A1 | 12/2010 | Fang et al. |
| 2014/0227237 | A1* | 8/2014 | June ...................... A61K 40/31 435/325 |
| 2018/0169146 | A1 | 6/2018 | Goldberg et al. |
| 2018/0177893 | A1 | 6/2018 | Angel et al. |
| 2018/0305705 | A1 | 10/2018 | Daly |
| 2019/0000995 | A1 | 1/2019 | Angel et al. |
| 2019/0000996 | A1 | 1/2019 | Angel et al. |
| 2019/0000997 | A1 | 1/2019 | Angel et al. |
| 2019/0008985 | A1 | 1/2019 | Angel et al. |
| 2019/0144883 | A1 | 5/2019 | Plank et al. |
| 2019/0307897 | A1 | 10/2019 | Angel et al. |
| 2019/0365923 | A1 | 12/2019 | Angel et al. |
| 2020/0108157 | A1 | 4/2020 | Angel et al. |
| 2020/0147239 | A1 | 5/2020 | Angel et al. |
| 2020/0247859 | A1 | 8/2020 | Shimomura et al. |
| 2020/0332004 | A1 | 10/2020 | Boyne et al. |
| 2021/0000974 | A1 | 1/2021 | Angel et al. |
| 2022/0290176 | A1 | 9/2022 | Kim et al. |
| 2023/0015146 | A1 | 1/2023 | Angel et al. |
| 2023/0086606 | A1 | 3/2023 | Plank et al. |

FOREIGN PATENT DOCUMENTS

| | | | |
|---|---|---|---|
| CN | 109553686 A | 4/2019 | |
| JP | 2004-530425 A | 10/2004 | |
| JP | 2006-526409 A | 11/2006 | |
| JP | 2007-295846 A | 11/2007 | |
| JP | 2011-167123 A | 9/2011 | |
| JP | 2019-528284 A | 10/2019 | |
| KR | 10-2018-0131577 A | 12/2018 | |
| KR | 10-2021-0065065 A | 6/2021 | |
| WO | 2016/197121 A1 | 12/2016 | |
| WO | 2017/028374 A1 | 2/2017 | |
| WO | WO-2018126116 A1 * | 7/2018 | ............ A61K 48/00 |
| WO | 2018/191722 A1 | 10/2018 | |
| WO | 2019/082721 A1 | 5/2019 | |
| WO | 2019/129851 A1 | 7/2019 | |
| WO | 2022/250430 A1 | 12/2022 | |

OTHER PUBLICATIONS

Notice of Allowance issued on Jan. 10, 2023, for corresponding Korean Patent Application No. 10-2020-0161549, along with an English machine translation (4 pages).

International Search Report issued on Aug. 29, 2022, for related International Patent Application No. PCT/KR2022/007377, along with an English translation (9 pages).

Written Opinion issued on Aug. 29, 2022, for related International Patent Application No. PCT/KR2022/007377 (6 pages).

International Search Report mailed Mar. 5, 2021, in connection with International Patent Application No. PCT/KR2020/016988, along with English translation.

PCT Written Opinion mailed Mar. 5, 2021, in connection with International Patent Application No. PCT/KR2020/016988.

Hu et al., "Chimeric antigen receptor (CAR)-transduced natural killer cells in tumor immunotherapy," Acta Pharmacologica Sinica, Sep. 7, 2017, vol. 39, pp. 167-176; cited in NPL Nos. 1 and 2.

Kakoki et al., "Altering the Expression in Mice of Genes by Modifying Their 3' Regions," Developmental Cell, Apr. 12, 4 2004, vol. 6, pp. 597-606; cited in NPL No. 1.

Yangbing Zhao et al., "Multiple Injections of Electroporated Autologous T Cells Expressing a Chimeric Antigen 5 Receptor Mediate Regression of Human Disseminated Tumor," Cancer Research, Oct. 5, 2010, vol. 70, pp. 9053-9061.

Ruocong Zhao et al., "DNAX-activating protein 10 co-stimulation enhances the anti-tumor efficacy of chimeric antigen 6 receptor T cells," OncoImmunology, Nov. 2, 2018, vol. 8, Article No. e1509173, 13 pages.

The extended European Search Report dated May 12, 2023 for corresponding European Patent Application No. 20893955.3, 7 pages.

Japanese Office Action dated Jun. 13, 2023 for corresponding Japanese Patent Application No. 2022-531074, 10 pages, with English Machine Translation.

Office Action dated Mar. 26, 2025 for corresponding Korean Patent Application No. 10-2022-0063733, along with an English translation (10 pages).

Setare Adibzadeh et al., "Enhancing Stability of Destabilized Green Fluorescent Protein Using Chimeric mRNA Containing Human Beta-Globin 5' and 3' Untranslated Regions", Avicenna Journal of Medical Biotechnology, vol. 11, No. 1, Jan.-Mar. 2019, pp. 112-117.

Nora Hosny et al., "3'UTR enhances hCD47 cell surface expression, self-signal function, and reduces ER stress in porcine fibroblasts", Xenotransplantation, vol. 28:e12641, 2021 (14 pages).

* cited by examiner

A.

Tx-CAR-NK cell injection ($3\times10^6$ cells each, i.v.)

2  4  7  9

0 Day

A549-Red-FLuc cell ($2\times10^6$ cells, i.v.)

B.  C.

*in vivo*  *ex vivo*

*in vivo* Lung (Day 72)  *Ex vivo* Lung (Day 102)

mRNA CONSTRUCT FOR PROTEIN EXPRESSION AND USE OF SAME

CROSS-REFERENCE TO RELATED APPLICATIONS

The present application is a Continuation-In-Part of International Patent Application No. PCT/KR2020/016988 filed Nov. 26, 2020, which is based on and claims priority to Korean Patent Application No. 10-2019-0152938 filed on Nov. 26, 2019, in the Korean Intellectual Property Office, the disclosures of which are incorporated herein by reference in their entireties.

TECHNICAL FIELD

The present invention relates to an mRNA construct capable of inducing the expression of a target protein with stable and high efficiency while maintaining the function of the target protein.

BACKGROUND ART

Over a few decades, there have been continuous change and advances in the methods for treating cancer. From 1800's to 1900's, methods such as surgery, chemotherapy, and radiation therapy were commonly practiced, but as their limitations started to come to light, in recent years, as immune-cell therapy, a cell therapy technique has been under development, which extracts immune cells from the body and enhances or modifies the cells via genetic engineering, before placing them back. Well-known examples of such a technique include tumor infiltrating lymphocytes (TIL), chimeric antigen receptor (CAR), T-cell receptor (TCR) techniques, and the like, and in particular, research and clinical trials using a CAR (chimeric antigen receptor), which is an artificial receptor using genetic recombineering, are underway. However, gene therapy or cellular therapy techniques using the above genetic engineering are facing multiple challenges from undesirable immune responses to safety issues, due to genes being incidentally introduced at random locations in the genome. In this regard, there are issues in transfected CAR-NK cells (chimeric antigen receptor natural killer cells) using DNA that the CAR gene is integrated in the genome or mutations occur, and therefore, safety cannot be secured. To address these issues, there has been an attempt to use transient transfected CAR-NK cells. However, in transient transfection using mRNA, instability of mRNA and low transfection levels and target protein expression levels act as hurdles, and thus, there has been no studies yet that have yielded positive result.

DISCLOSURE OF THE INVENTION

Technical Problem

To address the above issues, an aspect of the present invention provides an mRNA construct that can be used in transfection to enable a stable and effective target protein (or peptide) expression without genomic mutations within a cell.

Technical Solution

According to an aspect of the present invention, there is provided an mRNA construct, comprising: (a) a target protein or peptide coding region; (b) a 5'-β-globin UTR region upstream of the target protein or peptide coding region; and (c) a BGH region downstream of the target protein or peptide coding region.

According to one embodiment of the present invention, the 5'-β-globin UTR region may comprise a sequence of SEQ ID NO: 1. Also, according to another embodiment of the present invention, the BGH region may comprise a sequence of SEQ ID NO: 2.

According to one embodiment of the present invention, the mRNA construct may be for transient transfection.

According to another embodiment of the present invention, the target protein (a) may be a chimeric antigen receptor (CAR).

According to another embodiment of the present invention, the CAR may include an ectodomain capable of specifically binding to a target, a transmembrane (TM) domain penetrating a cell membrane, and an endodomain inducing intracellular signal transduction.

According to another embodiment of the present invention, the ectodomain may be an antibody fragment (ScFv) in which a light chain and a heavy chain are linked via a linker, and the endodomain may be CD28 and may further include DAP10 and/or CD3z.

According to another embodiment of the present invention, the ectodomain and TM domain of the CAR may be linked via a spacer, and the spacer may be Myc-Hinge.

According to another embodiment of the present invention, the mRNA construct may include Cap at the 5'-terminal and may include poly(A)tail at the 3'-terminal.

In addition, the present invention provides a recombinant vector including a base sequence of the mRNA construct, or a base sequence complementary thereto.

In addition, the present invention provides a transient transformant preparation method including the following steps:

(1) preparing the mRNA construct or the recombinant vector; and (2) introducing the mRNA construct or the recombinant vector into a cell.

According to one embodiment of the present invention, the step (2) may utilize electroporation and may preferably utilize the NEPA21 system. The electroporation using the NEPA21 system may be performed under a condition of 110 V to 200 V, and may be preferably performed under a condition of 110 V to 140 V, and more preferably under a condition of 110 V.

In the above preparation method, the cell may be a plant cell or an animal cell, but preferably may be an animal cell, and may be a natural killer cell (NK cell) among animal cells.

In addition, the present invention provides a transfected cell including the mRNA construct or the recombinant vector. The transfected cell may be a transient transfected cell. The transfected cell may be prepared by the above preparation method and express a target protein (or peptide) without DNA insertions in chromosomes. The target protein (or peptide) may be expressed for 3 days.

According to one embodiment of the present invention, the NK cell is a primary NK cell or a NK cell line, and the CAR-NK may undergo a transfection via the NEPA21 system. In addition, the above transfection may be performed under a condition of 110 V to 200 V.

Meanwhile, in a case in which the cell in the above preparation method is an NK cell, and the target protein encoded by the mRNA construct or recombinant vector introduced into the cell is a CAR, the transfected cell preparation method of the present invention may be utilized as a preparation method for a chimeric antigen receptor natural killer (CAR-NK) cell, wherein the transfection of the mRNA construct or the recombinant vector into the cell may be performed utilizing the NEPA21 system under a condition of 110 V to 200 V (preferably, 110 V for the NK host cell, and 200 V for the primary NK cell).

In addition, the present invention may provide a CAR-NK cell prepared by the above CAR-NK cell preparation method, and the CAR-NK cell thus prepared expresses a chimeric antigen receptor (CAR) without DNA insertions in chromosomes and thus, has high in vivo stability.

In addition, the present invention provides a cell therapy composition for treating a cancer, comprising the CAR-NK cell. The cancer may be a solid cancer, and the solid cancer may be a breast cancer and/or a lung cancer.

In addition, the present invention provides a cancer treatment method including a step of administering the above CAR-NK cell to a subject.

In addition, the present invention provides a use of the CAR-NK cell for the preparation of an anticancer agent.

Advantageous Effects

The mRNA of the present invention is stable and can be introduced into a cell to express a functional target protein over a long period, and is thus expected to be extremely useful in transfection techniques, and transient transfection techniques in particular. In addition, the transfected CAR-NK prepared by the method of the present invention shows excellent cancer cell cytotoxicity and expresses CAR without genetic insertions in the genome of NK cells, and thus has secured in-vivo safety, and thus can be advantageously utilized in anticancer pharmaceutical compositions and an anticancer immunotherapy targeting solid cancer.

Figure 16:
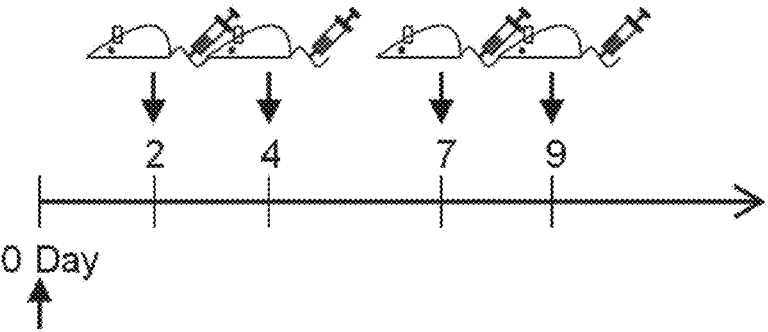
Figure 16:
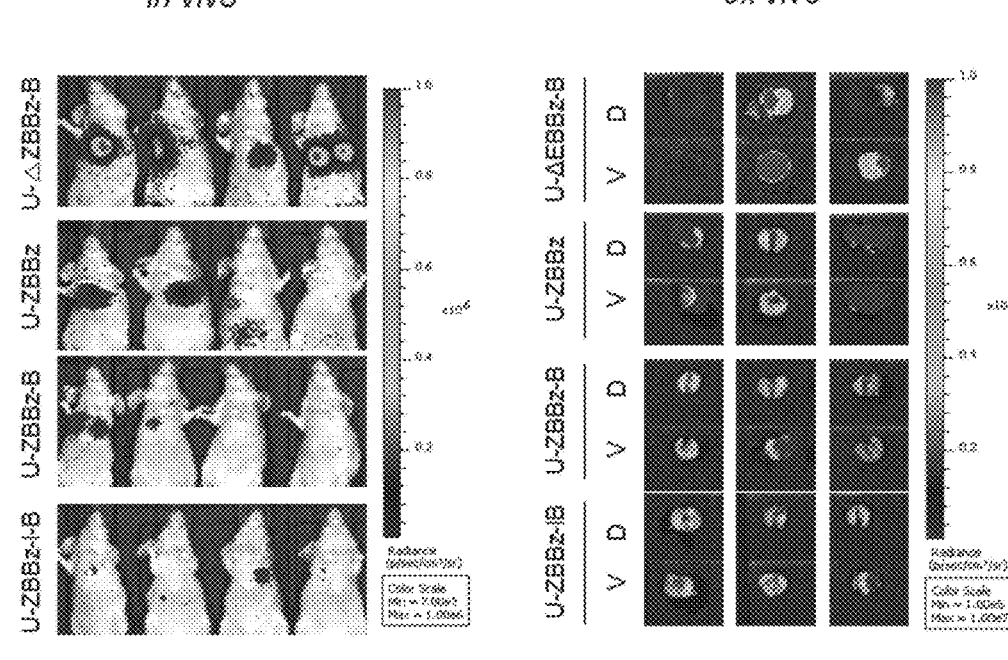
Figure 16:
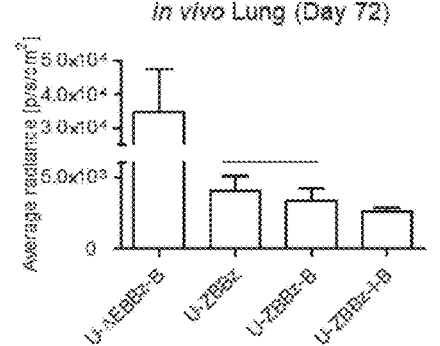
Figure 16:
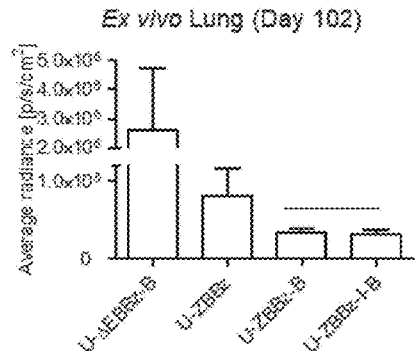

A of FIG. 16 is a schematic diagram of an in-vivo experiment schedule in mice. B of FIG. 16 is a diagram confirming the death rate of A549 cells injected intravenously when mRNA constructs 1 to 4 were injected into mice in-vivo. C of FIG. 16 is a diagram confirming the death rate of lung cells in ex-vivo after mRNA constructs 1 to 4 were injected into mice.

Figure 17:
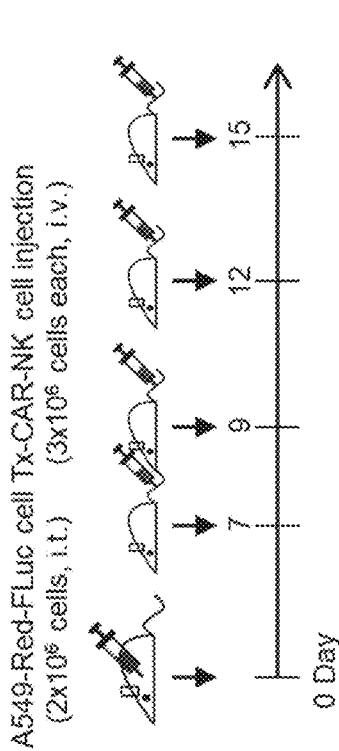
Figure 17:
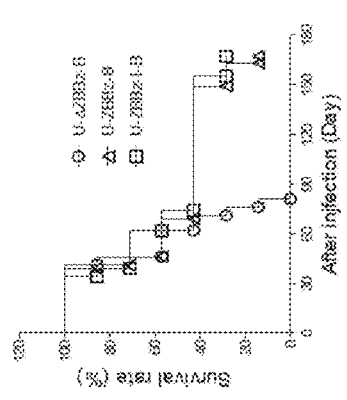
Figure 17:
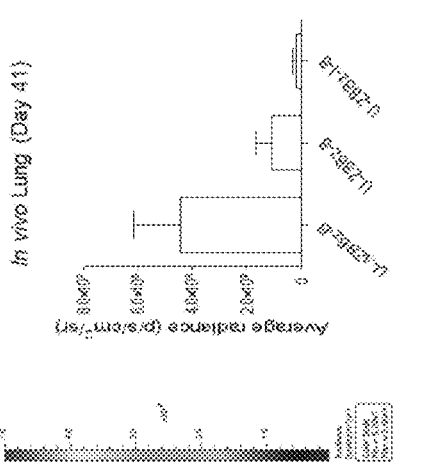
Figure 17:
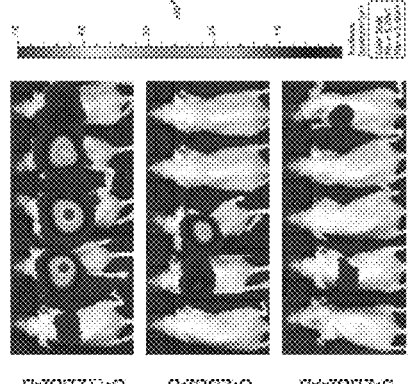

A of FIG. 17 is a schematic diagram of an in-vivo experiment schedule in mice. B of FIG. 17 is a diagram confirming the death rate of A549 cells directly injected into the lungs when mRNA constructs 1 to 3 were injected into mice. C of FIG. 17 is a diagram schematically showing the survival curve of the mouse after injection of mRNA constructs 1 to 3 into the mouse.

Figure 18:
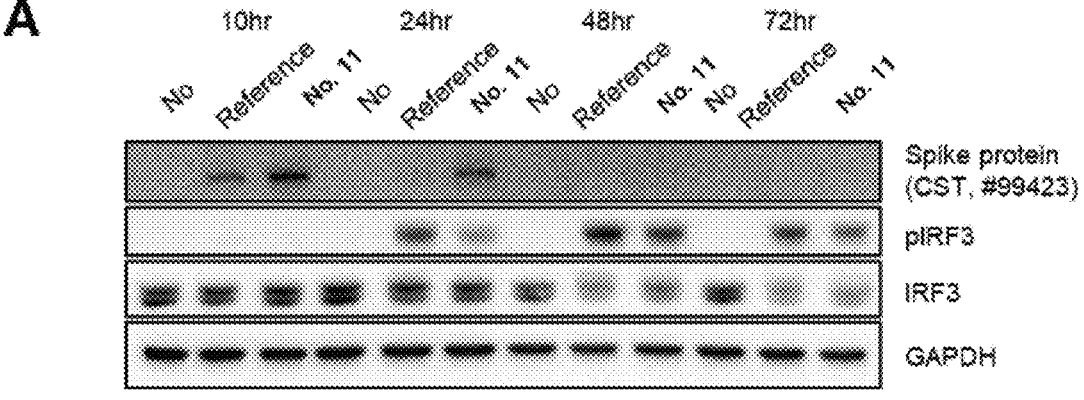
Figure 18:
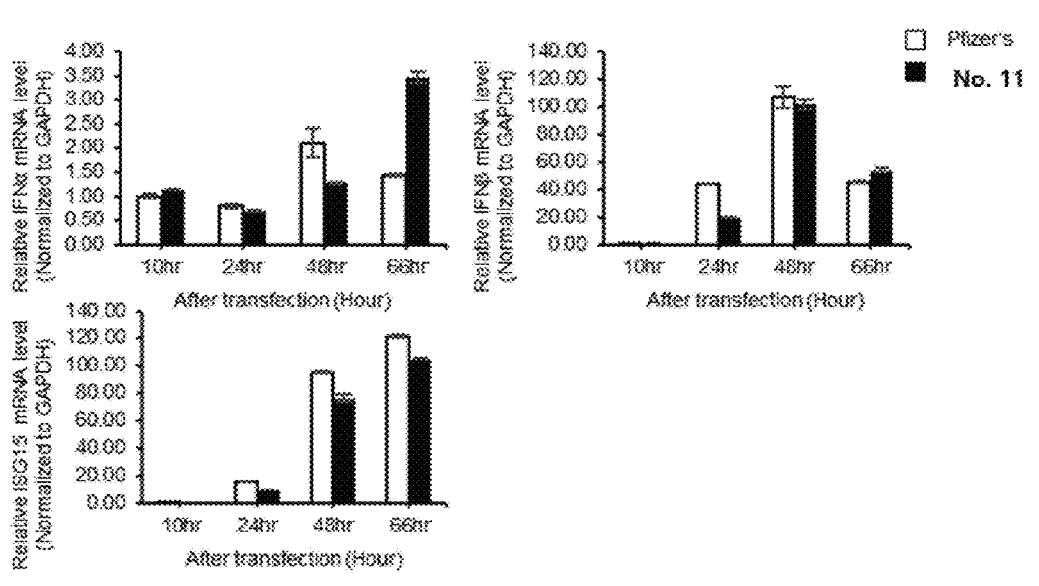

A of FIG. 18 shows the expression level of the spike protein in HEK-293T cells which are transduced with the Pfizer-BioNtech's COVID19 mRNA vaccine BNT162b2 and mRNA construct No. 11. B of FIG. 18 shows the expression level of the genes related to innate immunogenicity in HEK-293T cells which are transduced with the Pfizer-BioNtech's COVID19 mRNA vaccine BNT162b2 and mRNA construct No. 11.

MODE FOR CARRYING OUT THE INVENTION

The present inventors identified an mRNA construct that is structurally stable and when injected into a cell, can actively induce the expression of a functional target protein for a long period of time, thereby completing the present invention.

The present invention provides an mRNA construct, comprising: (a) a target protein or peptide coding region; and (b) an IRES region downstream of the target protein or peptide coding region.

The IRES region may comprises a sequence of SEQ ID NO: 3.

Also, the mRNA construct of the present invention may further comprise a 5'-β-globin UTR region upstream of the target protein or peptide coding region.

The 5'-β-globin UTR region may comprise a sequence of SEQ ID NO: 1.

Also, the mRNA construct of the present invention may further comprise a BGH region downstream of the target protein or peptide coding region.

The BGH region may comprise a sequence of SEQ ID NO: 2.

The IRES region may be included either i) in between the target protein or peptide coding region and the BGH region, or ii) downstream of the BGH region.

The mRNA construct of the present invention may further comprise a 5'-Cap and a 3'-Poly A tail region.

In the present invention, the term "IRES (internal ribosome entry site)" refers to an internal ribosome entry site or ribosome binding site, which is known to form a loop structure on mRNA and initiate translation in a cap-independent mechanism. Using the same to position IRES between two or more genes to prepare a single vector can express each of two genes simultaneously on a single mRNA. In this context, insertion of IRES region in order to induce the expression of a target protein is widely utilized in genetic recombination technology. However, the present inventors have confirmed that when the loop structure of IRES is located at 3' UTR of mRNA, the mRNA is structurally stable and can express a target protein with high efficiency. In particular, it was found that the RNA containing IRES-BGH sequence at 3' UTR has higher structural unity, stability, and protein expression efficiency than RNA containing BGH-IRES sequence.

The present inventors used the IRES region of encephalomyocarditis virus (EMCV) for IRES in the mRNA construct investigation.

Meanwhile, for enhancement in mRNA stability and protein expression efficiency, the location and order of IRES region are important. The present inventors have confirmed that mRNA stability and protein expression efficiency are lower when the IRES region is included in 5' UTR, than when the IRES region is included in 3' UTR. In addition, the present inventors have confirmed that even when the IRES is located at 3' UTR, mRNA stability and protein expression efficiency are lower when IRES is positioned in a reverse direction, than when IRES is positioned in a forward direction. From here, it could be confirmed that not only the ring structure of IRES, but also an organic combination of the position at which the ring structure is positioned (3'UTR) and its following BGH region, etc. contributes to an increase in mRNA stability and translation efficiency.

The 5'-β-globin UTR region refers to an untranslated region present upstream of the β-globin coding gene, that is, at the front of the 5'-end of the β-globin coding gene.

In the present invention, the term "BGH" refers to bovine growth hormone (bGH), which is a polyadenyl signal of bGH. The present inventors have confirmed, through experiments, that the 5'-β-globin UTR region present in the mRNA construct increases the mRNA stability by about 36%, and the BGH region located at 3' UTR increases the mRNA stability by about 20%.

The mRNA construct of the present invention is for use in transfection, and preferably transient transfection, that expresses a target protein for a predetermined time without genetic insertions in chromosomes of a host cell. Although it is important that the mRNA is structurally stable that a protein can be expressed with high efficiency for a long time, it is an essential condition to achieve an ultimate goal of transfection that a protein successfully expressing the inherent function of a target protein can be expressed with high efficiency.

In this context, the present inventors have prepared a transient CAR-NK cell by transfecting a NK cell with a chimeric antigen receptor (CAR) as the target protein expressed by the above-described mRNA construct, and have confirmed the cancer cell cytotoxicity of the transient CAR-NK cell. As a result, it could be confirmed that the protein expression rate of the mRNA construct and the cancer cell cytotoxicity of the NK cell transfected with the mRNA construct are in a proportional relationship with respect to each other, and the mRNA construct of the present invention does not affect the inherent function of the target protein.

In the present invention, the term "UTR (untranslated region)" is also known as untranslated region, and the portion in an mRNA chain that does not serve as the template of protein gene, that is, untranslated portion, and the untranslated portion of mRNA, and generally, the upstream of coding region is referred to as 5' UTR, and the downstream thereof as 3' UTR.

Generally, in the UTR, there are a 5 UTR (5 untranslated region) and a 3 UTR (3 untranslated region), and the 5 UTR refers to the 5' terminal region and the 3 UTR refers to the 3' terminal region. The 3 UTR is known as an important regulatory element in messenger RNA (mRNA) of eukaryotes, and the 3' UTR refers to a translation terminator that contributes to the stability of mRNA in prokaryotes. In addition, it has been reported that an untranslated region (UTR) in mRNA plays a pivotal role in regulating both mRNA stability and mRNA translation.

It is known that 5' UTR motifs, for example, an upstream open reading frame (uORF) or an internal ribosomal entry site (IRES) is involved in gene regulation, in particular, translation initiation, but the function of IRES located at 3' UTR has been unknown.

It is known that through RNA-binding proteins and interactions therewith, UTR influences not only mRNA stability and intracellular localization, but also translation initiation, elongation, and termination. According to a particular motif within a UTR, mRNA turnover rate may be increased or decreased.

The present inventors added UTRs such as an upstream sequence of β-globin gene at 5' terminal, and a poly-A sequence and the bovine growth hormone (BGH) sequence at 3' terminal to the mRNA construct of the target protein chimeric antigen receptor (CAR) and the spike protein of COVID19 virus, and confirmed that the stability and expression levels of the mRNA construct was enhanced in the host cell.

Meanwhile, when the target protein of the mRNA construct of the present invention is CAR, high cancer cell cytotoxicity is shown when injected into NK cells, and therefore, the mRNA construct of the present invention may be used in the preparation of CAR-NK cells. In the present invention, the mRNA construct with its target protein being CAR is separately referred to as "CAR mRNA". In the present invention, the CAR mRNA may be understood as including a functional region that increases a protein expression rate from mRNA. Specifically, the CAR mRNA may include all of a region inducing ribosomes, a region involved in translation initiation or translation promotion of mRNA, a region involved in extranuclear transport of mRNA, a domain involved in binding with respect to endoplasmic reticulum membranes, a domain containing an endoplasmic reticulum-containing signal (ER-containing signal) sequence, and a region containing an endoplasmic reticulum signal sequence.

The present invention provides a recombinant vector including a DNA base sequence corresponding or complementary to the above mRNA. The vector of the present invention is an expression vector, and the expression vector refers to a genetic construct containing essential regulatory elements operably linked to an insert so that the insert can be expressed within a cell. The above expression vector may be prepared and purified utilizing standard recombinant DNA techniques. The expression vector is not limited to any particular kind as long as it serves the function of expressing a desired gene and producing a desired protein in various host cells of prokaryotes and eukaryotes, but preferably is a vector capable of producing a target protein in large volumes while containing a promoter expressing a potent activity and high expression levels. The expression vector preferably includes at least a promotor, an initiation codon, a gene coding a desired protein, and a stop codon terminator, but is not limited thereto. Other than the aforementioned components, the expression vector may include a DNA coding a signal peptide, an enhancer sequence, untranslated regions on the 5 and 3 sides of a desired gene, a selection marker region, or a cloning unit, etc. but is not limited thereto. Also, the expression vector refers to an expression cassette in which one or more transcriptional regulatory regions essentially containing a coding sequence and a promotor are operably linked together, or to a vector containing the expression cassette. The target protein, which is a protein serving as a target to be produced utilizing a protein secretion mechanism, or a protein sought to be produced in large volumes by one of ordinary skill in the art, refers to any protein which can be expressed in a transformant by inserting a polynucleotide coding the corresponding protein in a recombinant expression vector. For example, the target protein or peptide may be hormones, hormone analogs, enzymes, enzyme inhibitors, receptors and receptor fragments, antigens and antigen fragments or analogs, antibodies and antibody fragments, monoclonal antibodies, structural proteins, toxin proteins, their parts, or fused proteins whereby their parts or their entirety are fused.

In the present invention, a chimeric antigen receptor (CAR) and a spike protein of the COVID19 virus were used as the target protein or peptide.

Also, the present invention provides a transformant, wherein the mRNA construct is introduced into a host cell. The host cell indicates any type of cell capable of producing a protein by receiving the mRNA construct, and may be an animal cell, a plant cell, or a cell of a microorganism. In the present invention, immune cells, particularly NK cells, were used as the host cells.

The present invention provides an NK cell containing a chimeric antigen receptor (CAR) mRNA, wherein the NK cell is a chimeric antigen receptor natural killer (CAR-NK) cell, which may be a cell transfected with the CAR mRNA or the recombinant vector via the NEPA21 system.

Meanwhile, transfection or transduction refers to introducing an exogenous DNA into a cell. Transfection may be performed by various methods known in the corresponding field, such as calcium phosphate-DNA copre-cipitation method, DEAE Dextran-mediated transfection method, polybrene-mediated transfection method, electroporation method, microinjection method, liposome fusion method, lipofectamine, and protoplast fusion method. In addition, transfection refers to delivering a gene into a cell by using a virus or virus vector particle by means of infection. In the present specification, transfection and transduction may be interchangeably used, and preferably interpreted, in a wider sense, as transformation by delivering an exogenous gene in a host cell, and cells into which an exogenous gene is introduced by transfection or transduction is referred to as a transformant.

Meanwhile, transfection is distinguished as stable transfection when the introduced exogenous gene is an independently cloning form or inserted in a chromosome DNA of a host cell, or as a transient transfection when it is not.

The present invention is an mRNA construct provided to transfection, which has no DNA insertions in chromosomes of a host cell and has no risk of mutations, and which disappears in vivo within a few days, and has thus a high in-vivo stability, and the mRNA construct may be provided to transient transfection in particular.

In the present invention, transformation or transfection is performed by electroporation using NEPA21 super electroporator (Negagene, Japan). In addition, the present invention uses a transient transfection method or a transient transformation method. The transient expression is rapidly being used as a selection system for rapid mammalian protein production. Flexibility of transient transfection enables rapid demonstration from the concept of the present protein, and numerous different proteins can be simultaneously or continuously produced. In this regard, Rodrigo Vazquez-Lombardi et al (Transient expression of human antibodies in mammalian cells, Nat Protoc. 2018 January; 13(1) 99-117) reports that transient mammalian expression systems are capable of producing recombinant antibodies of 100 mg/liter or more at a reasonable cost.

Also, the present invention provides a cell therapy composition comprising the transformant.

The cell therapy composition of the present invention includes a pharmaceutically or pharmacologically acceptable carrier. The pharmaceutically or pharmacologically acceptable carrier of the present invention is commonly used in preparations, and the cell therapy composition of the present invention may further include suspensions, preservatives, etc. other than the above-mentioned ingredients. Appropriate pharmacologically acceptable carriers or preparations are described in detail in Remington s Pharmaceutical Sciences (19th ed., 1995).

The cell therapy composition of the present invention, when used in the form of administration to a subject, may be formulated before use, into preparations in a unit dose form that is appropriate for administration into a patient's body, by common methods in the pharmaceutical field, such as intravenous injection, subcutaneous injection, intramuscular injection, and the like.

A preferable dose of the cell therapy composition of the present invention may vary depending on a patient's state, body weight, severity of disease, and drug form, and administration route and period, but may be appropriately selected by a person skilled in the art.

The cell therapy composition of the present invention may be used through an injection ampoule. The injection ampoule may be prepared by mixing with an injection solution immediately before use, and for the injection solution, a saline solution, glucose, mannitol, Ringer's solution, etc. may be used. The pharmaceutical composition or preparation of the present invention thus prepared may be administered in a form of a mixture with cells used for transplantation and other uses, by using an administration method that is commonly used in the corresponding field. The actual amount of an active ingredient administered shall be determined in view of other factors such as a disease to be treated, severity of the disease, an administration route, a patient's body weight, age, and sex.

Hereinafter, the present invention will be described in more detail through the examples. However, the following examples are provided merely to illustrate the present invention and as such, should not be construed as limiting the scope of the present invention.

<Example 1> CAR mRNA Structure

Figure 1:
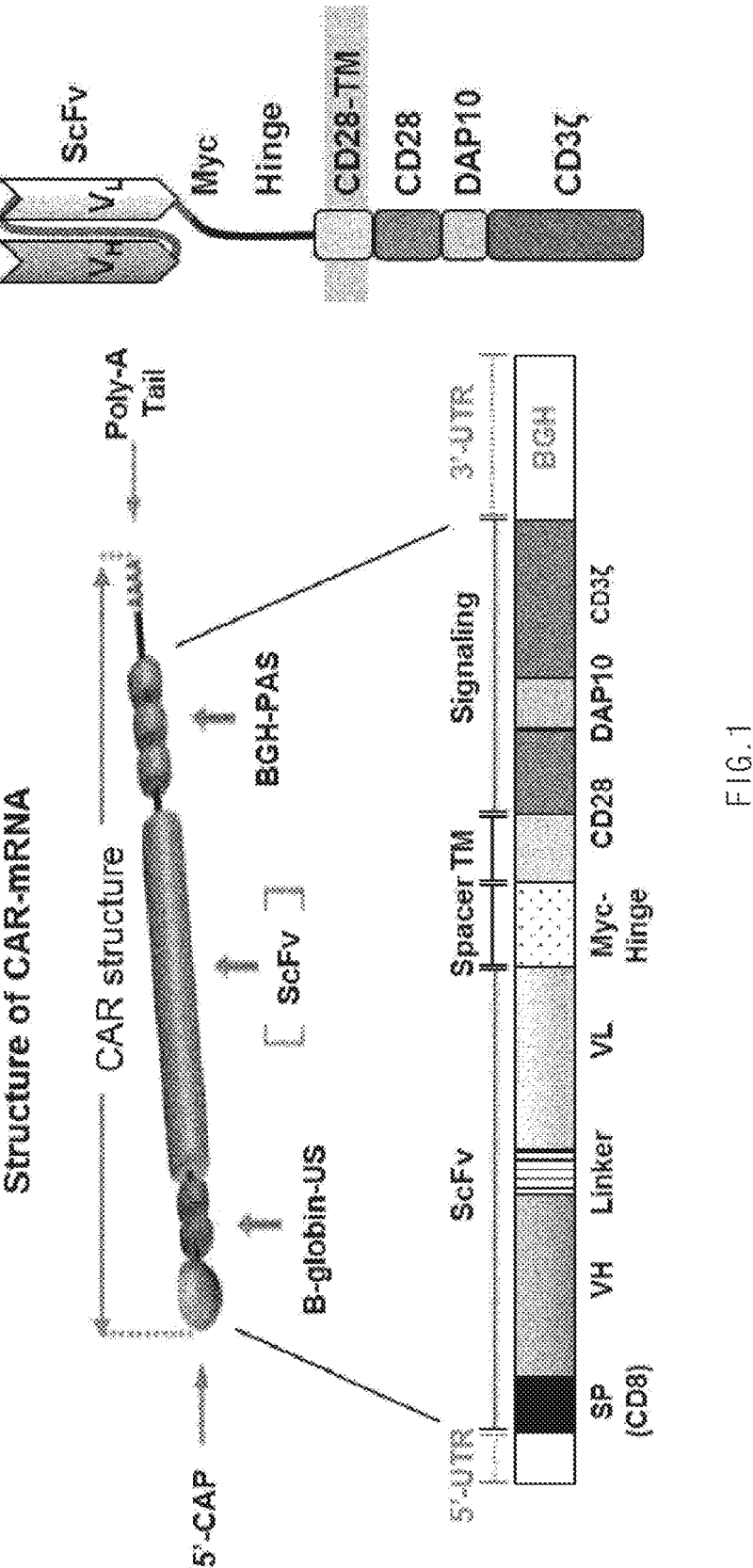
FIG. 1 shows the structure of CAR-mRNA and the domain and motif constructs of CAR.

Chimeric antigen receptor (CAR) used in the present invention consists of an ectodomain recognizing a target, an endodomain inducing intracellular signal transduction (cell signaling), a spacer (Myc-Hinge) connecting the ectodomain and imparting flexibility, and a transmembrane (TM) domain that passing through cellular membranes. The CAR ectodomain of the present invention consists of a ScFv composed of a heavy chain and a light chain connected via a linker, and the endodomain adopts CD28 and DAP10 as a co-activator and is a third-generation CAR construct composed of CD3z responsible for cytotoxic signaling as shown in FIG. 1.

<Example 2> Optimization of Transfection

Figure 2:
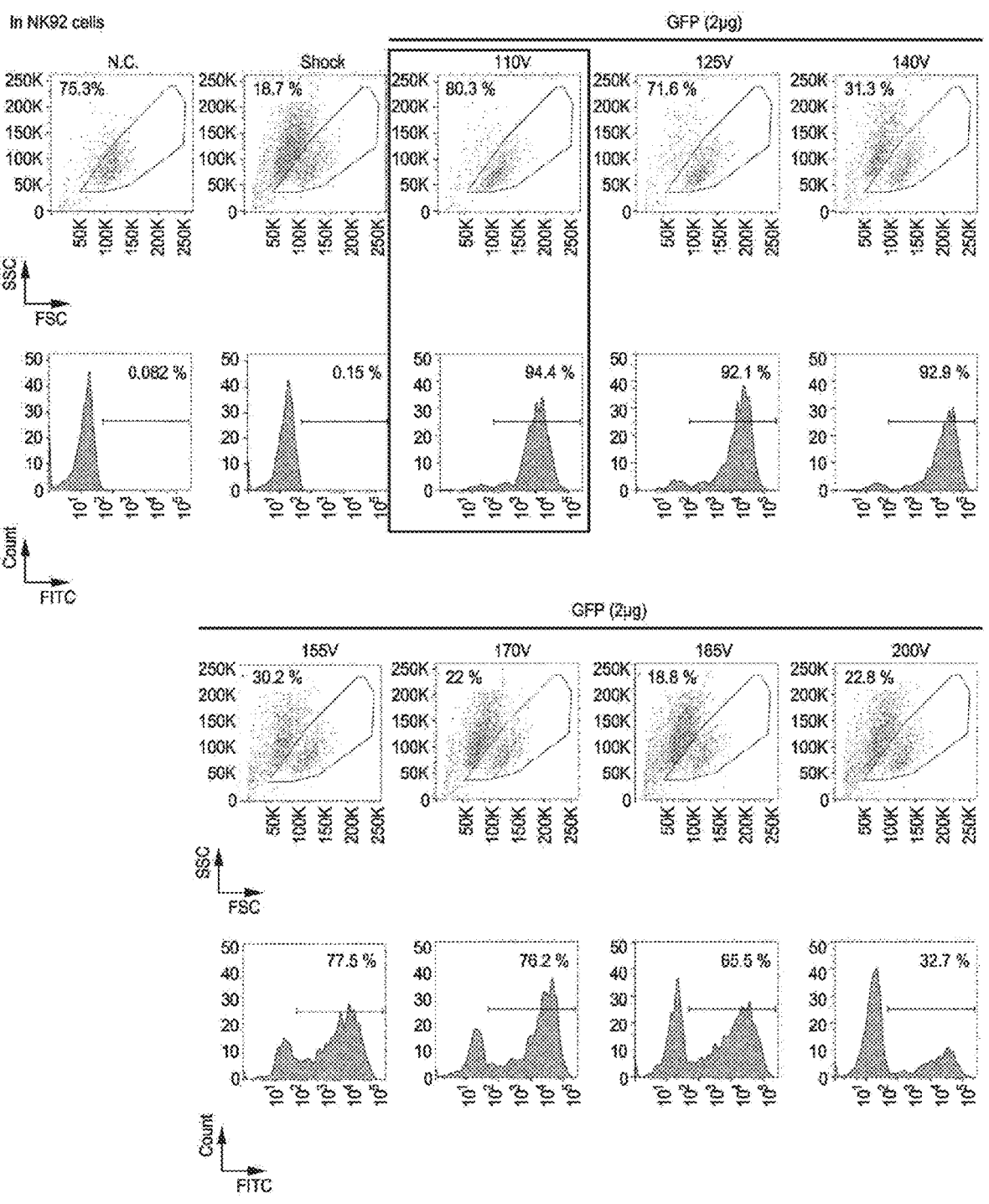
FIG. 2 shows a result of transfection optimization, and a result of establishing transfection conditions for NK92 cells using the NEPA21 system.

To establish optimal transfection conditions, GFP expressions were observed from transfection performed using the NEPA21 system while varying the voltage from 110 V to 200 V using 2 μg GFP-mRNA in 1×10⁶ cells (FIG. 2), and as a result, along with increased voltage, lower cell viability was observed. In NK92 cell lines (NK cell line, natural killer cell cell line) GFP expressions of 90% or more were observed at 110 V, 125 V, and 140 V, and in the CAR-mRNA transfection efficiency evaluation, the highest cell viability and expression rate were observed at 110 V. Increasing the amount of mRNA used per cell in NK92 1×10⁶ to 5 μg from 2 μg results in increased expression levels, and CAR expressions were observed up to 3 days post transfection. After scaling-up based thereon, expression levels were good when transfected with 20 μg mRNA per cell in 1×10⁷ and were found to be sustained for 3 days post transfection, which is the same duration as in 1×10⁶ cells.

Figure 3:
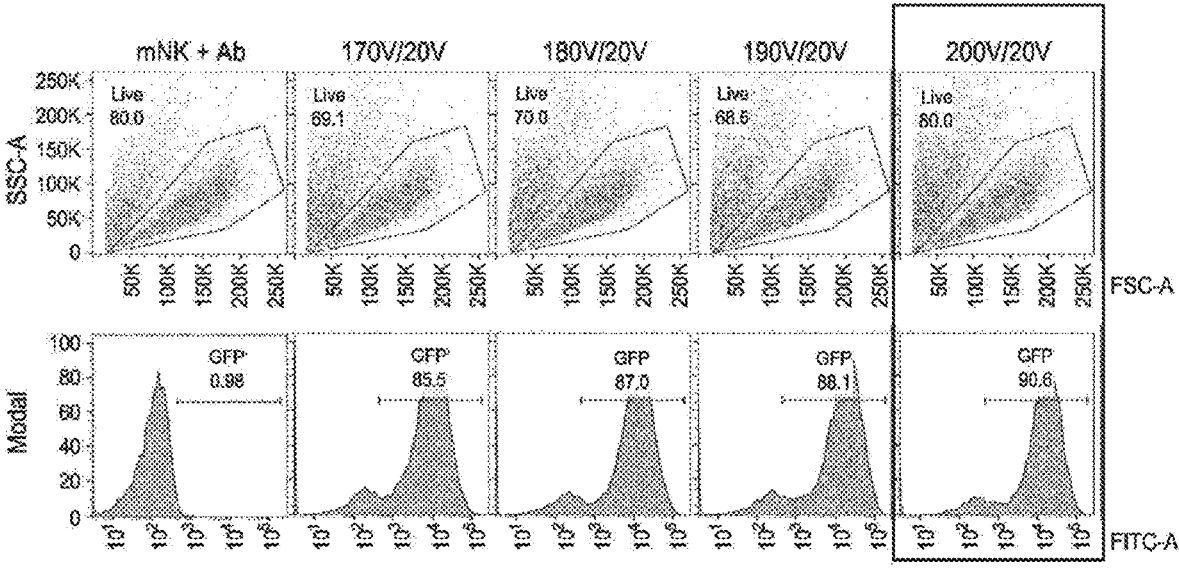
FIG. 3 shows a result of transfection optimization, and a result of establishing transfection conditions for primary NK cells cells using the NEPA21 system.
Figure 3:
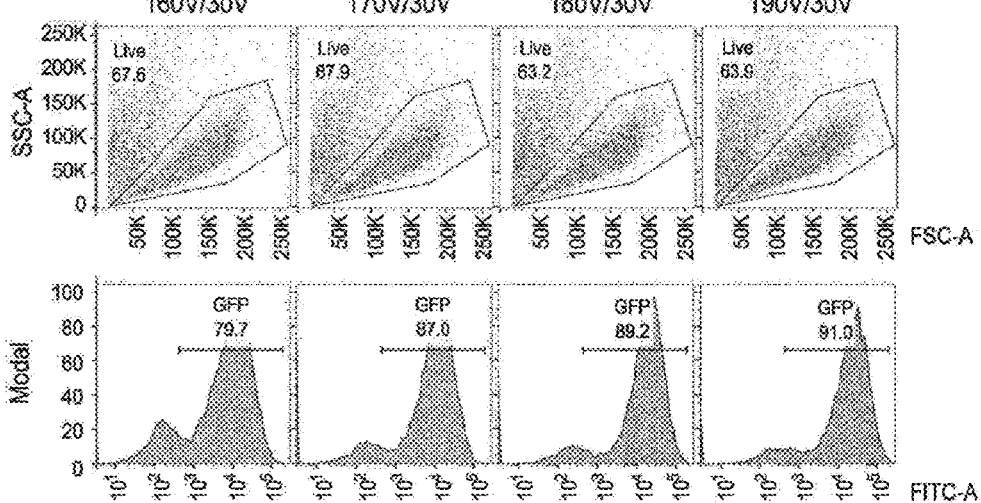

Using the NEPA21 system, 5 μg GFP-mRNA was transfected into primary NK 1×10⁶ cells obtained by treating and aging monocytes obtained by CD3-depletion from umbilical cord blood with hydrocortisone and cytokines (IL15, IL21) for 7 days or more. As a result, high transfection efficiency was shown under at condition of 190 V and 200 V (FIG. 3). As shown above, in the evaluation of CAR-mRNA transfection efficiency, the highest efficiency was observed at 200 V.

<Example 3> Characterization of Time-Dependent CAR Expressions in Transient CAR NK92 Cell and Stable CAR NK92 Cell Using the NEPA21 system, CAR mRNAs having anti-CEACAM6 scFv, cotinine-tagged antibody with respect to an antigen, and anti-cotinine scFv capable of recognizing the same were obtained by in-vitro transcription. The obtained mRNA of anti-CEACAM6-CAR and anti-cotinine-CAR were transfected in NK92, and CAR expression profiles over time, and cytotoxicity of transient CAR-NK cells were examined. CAR expression levels in NK92 cells according to scFV sequence with respect to cotinine and CEACAM6 were examined. As a result, anti-CEACAM6-CAR sustained a high expression level of 90% or more up to 48 h post mRNA introduction, and anti-continine-CAR showed an expression level of 70% or more up to 16 h post mRNA introduction, and the expression sustained for up to 2 days. In addition, using conjugate molecules of EGFR, cytolytic activity of Cotinine-CAR-NK cells was measured. As a result, it was found that cytotoxicity is high when the protein expression is high after CAR mRNA transfection, and cytotoxicity decreases along with a decrease in expression level thereafter (FIG. 4 and FIG. 5).

On the other hand, the nucleotide sequences of the gene constructs encoding the anti-CEACAM6-CAR and anti-cotinine-CAR designed as described above are respectively inserted into the lentiviral vector, and was transduced into HEK293T cells with a viral packaging vector (PMDLg/RRE, RSV/REV, VSVG) to obtain lentiviruses expressing anti-CEACAM6-CAR and anti-cotinine-CAR. The obtained anti-CEACAM6-CAR and anti-cotinine-CAR-expressing lentiviruses were respectively infected to NK92 cells by spinoculation method (360 g, 90 min, RT) in order to produce stable CAR-NK cells.

For the stable CAR-NK cells prepared as described above, the expression pattern (expression rate and duration of expression) and cytotoxicity of the CAR over time were confirmed in the same manner as in the transient CAR-NK cells.

Figure 4:
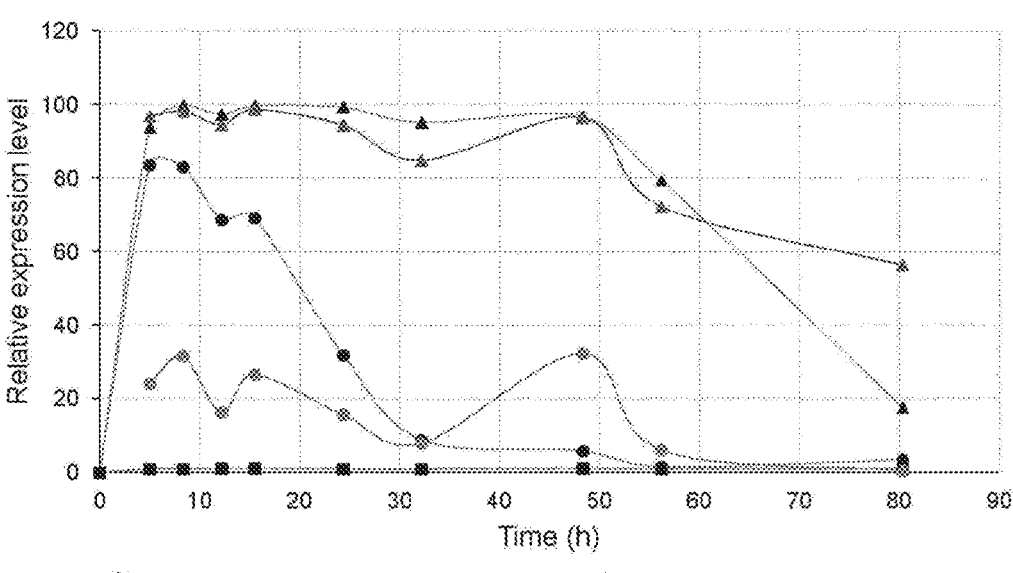
FIG. 4 shows a result of characterization of CAR expressions over time in transient CAR NK92 cells and stable CAR NK92 cells.
Figure 5:
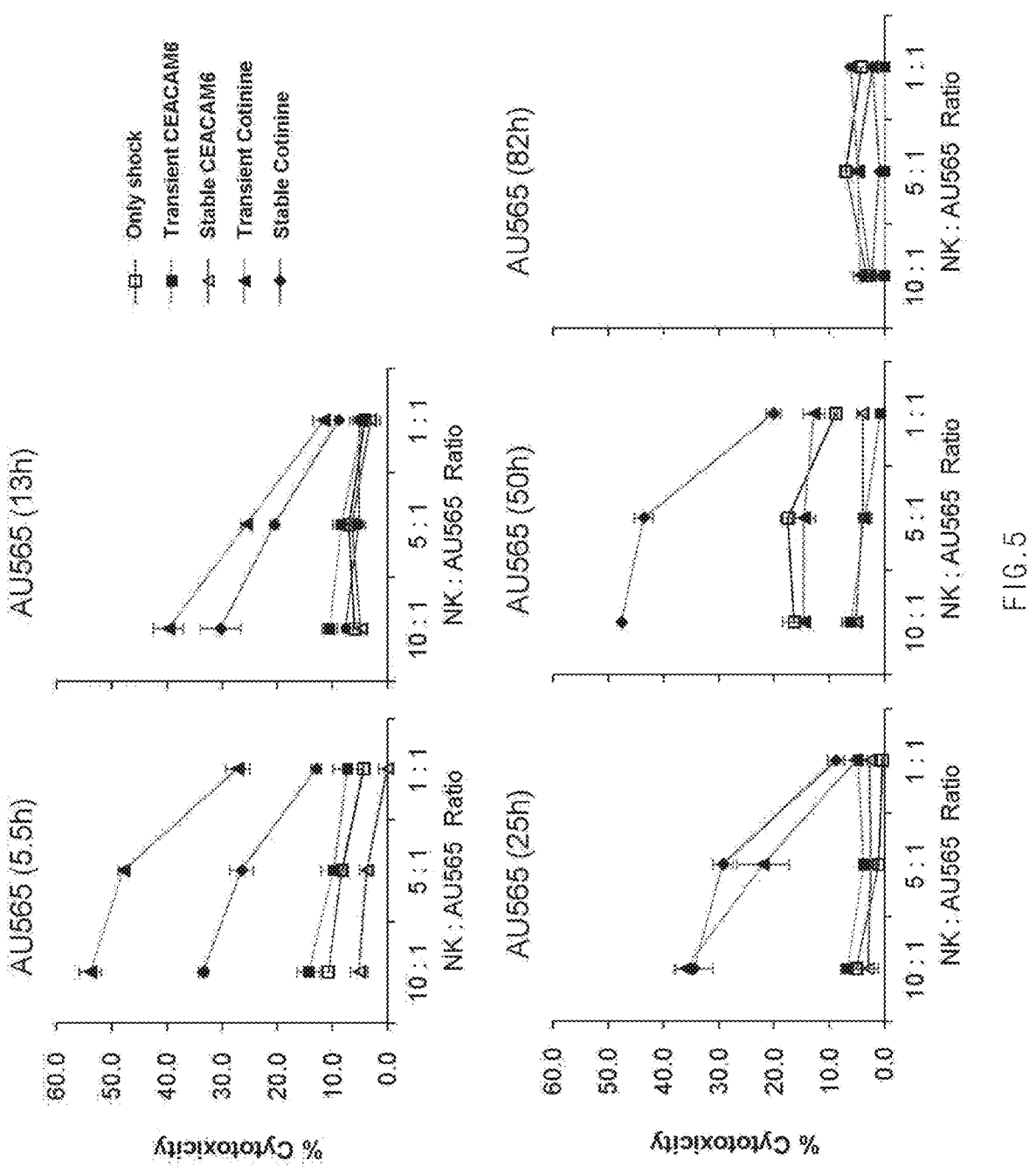
FIG. 5 shows a result of characterization cancer cell cytotoxity over time with respect to transient CAR NK92 cells and stable CAR NK92 cells.

As a result, as shown in FIG. 4, in the case of anti-CEACAM6-CAR, as in transient CAR-NK cells, a high expression rate of 90% or more was maintained up to 48 hours, and the expression continued for 4 days. In the case of anti-cotinine-CAR it was confirmed that the expression rate of less than 40% persisted for 2 days. In addition, cytotoxicity, as shown in FIG. 5, was confirmed to exhibit the same pattern as the protein expression of CARs as in transient CAR-NK cells.

<Example 4> Confirmation of Enhancement in Expression Levels and Cancer Cell Cytotoxicity of Chimeric Antigen Receptor Containing DAP10

Figure 6:
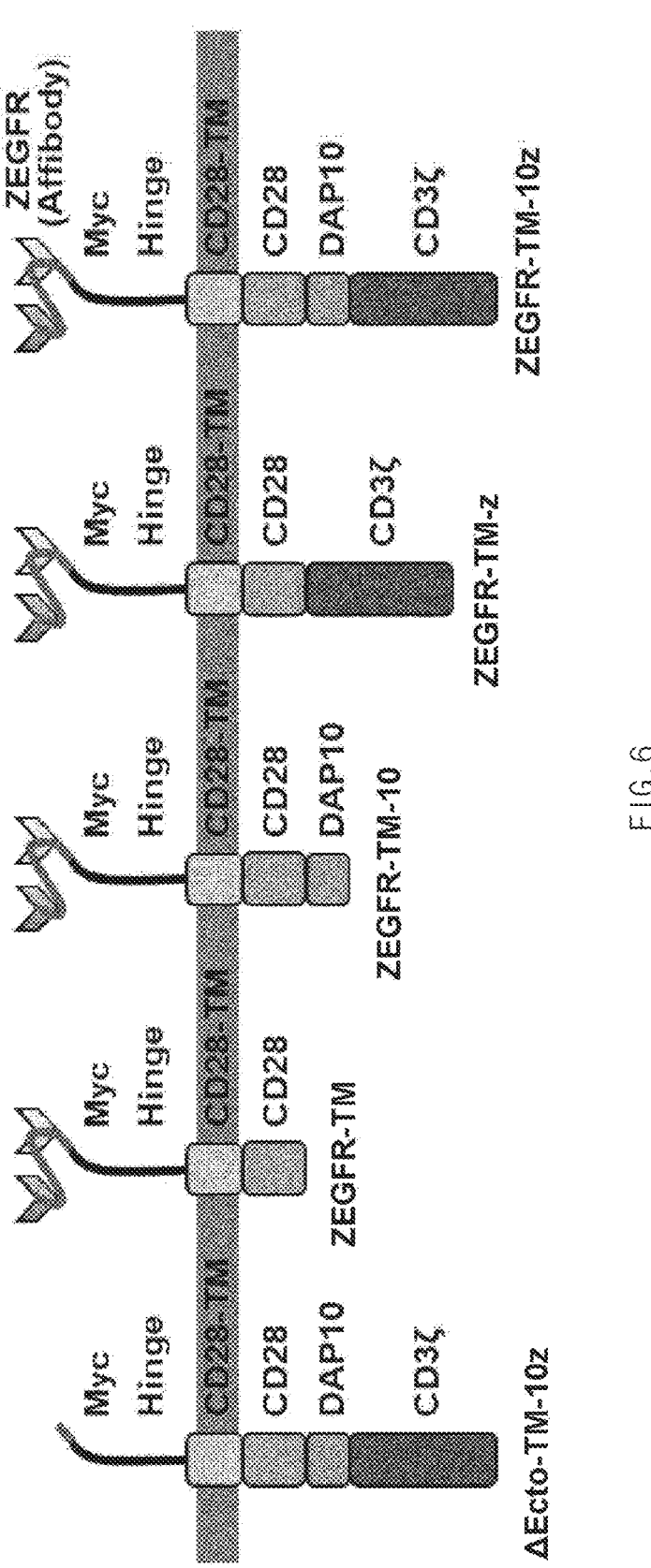
FIG. 6 shows vector constructs or domains and motifs constituting CAR for experiments for characterization of cancer cell cytotoxicity and expression rates of a chimeric antigen receptor containing DAP10, FIG. 7, in association with FIG. 6, shows the characterization of CAR expression levels depending on the presence of DAP10 when CAR mRNA transfection using FACS.
Figure 7:
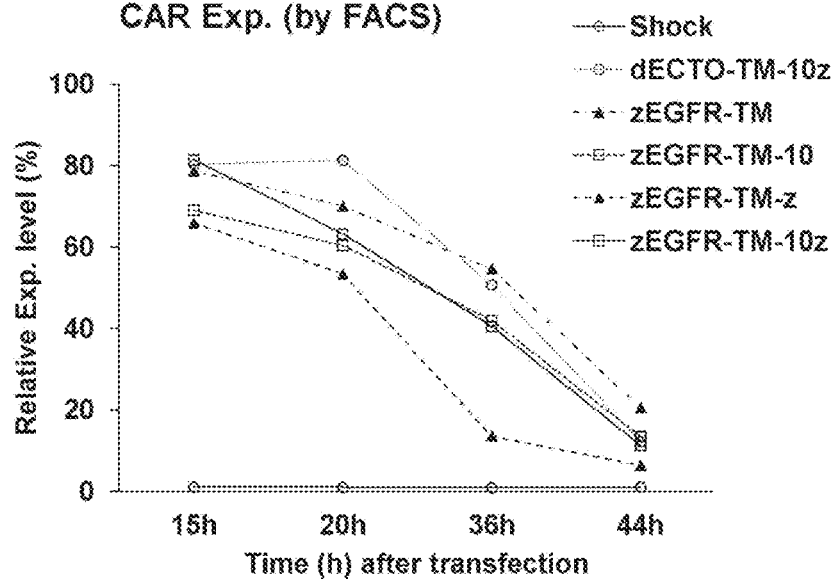
Figure 8:
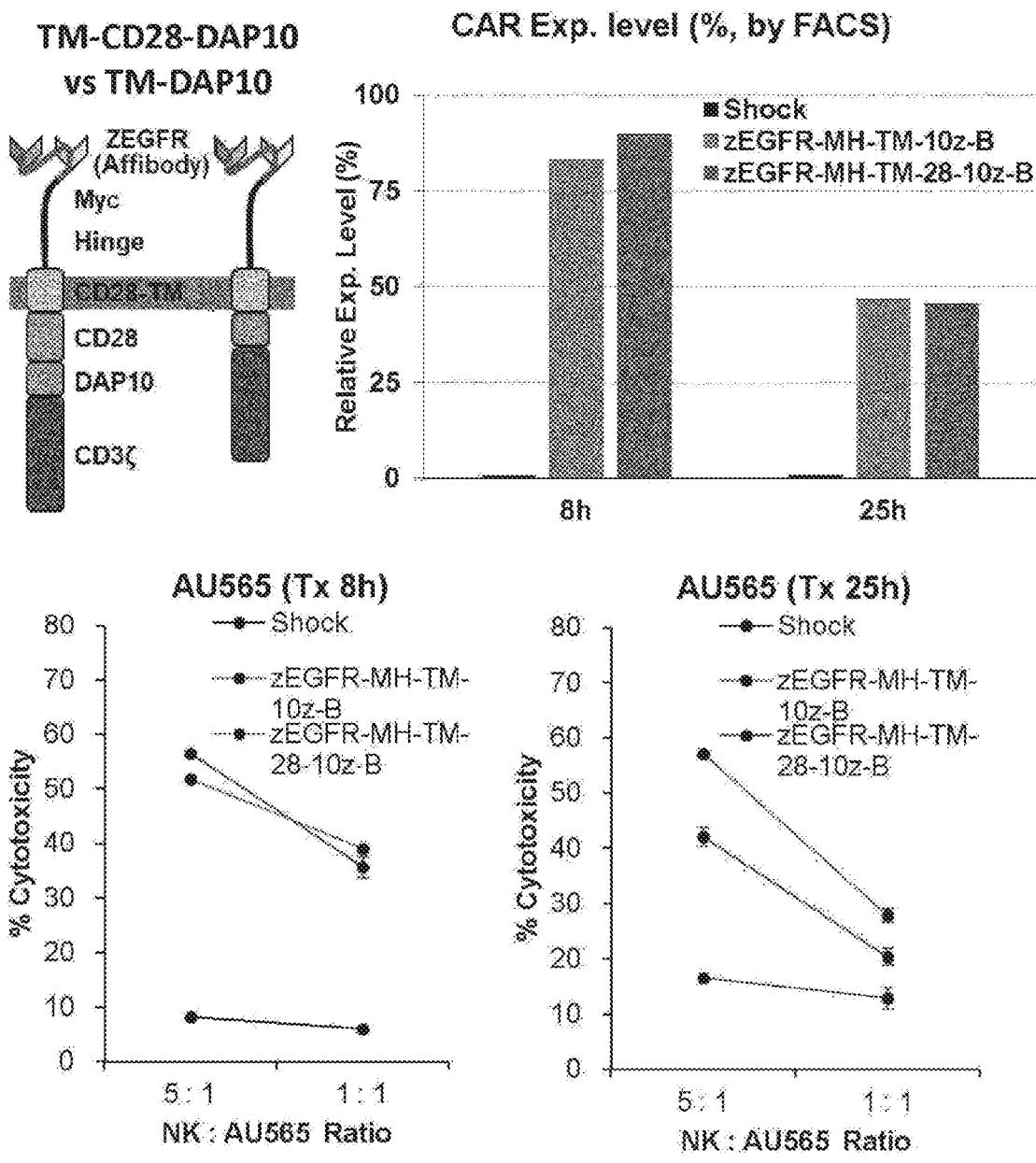
FIG. 8 shows a result of differences in CAR expression levels and cytotoxicity according to the form of a third-generation CAR with two co-activators (CD28, DAP10) and a second-generation CAR with one co-activator (DAP10) in the CAR structure.
Figure 9:
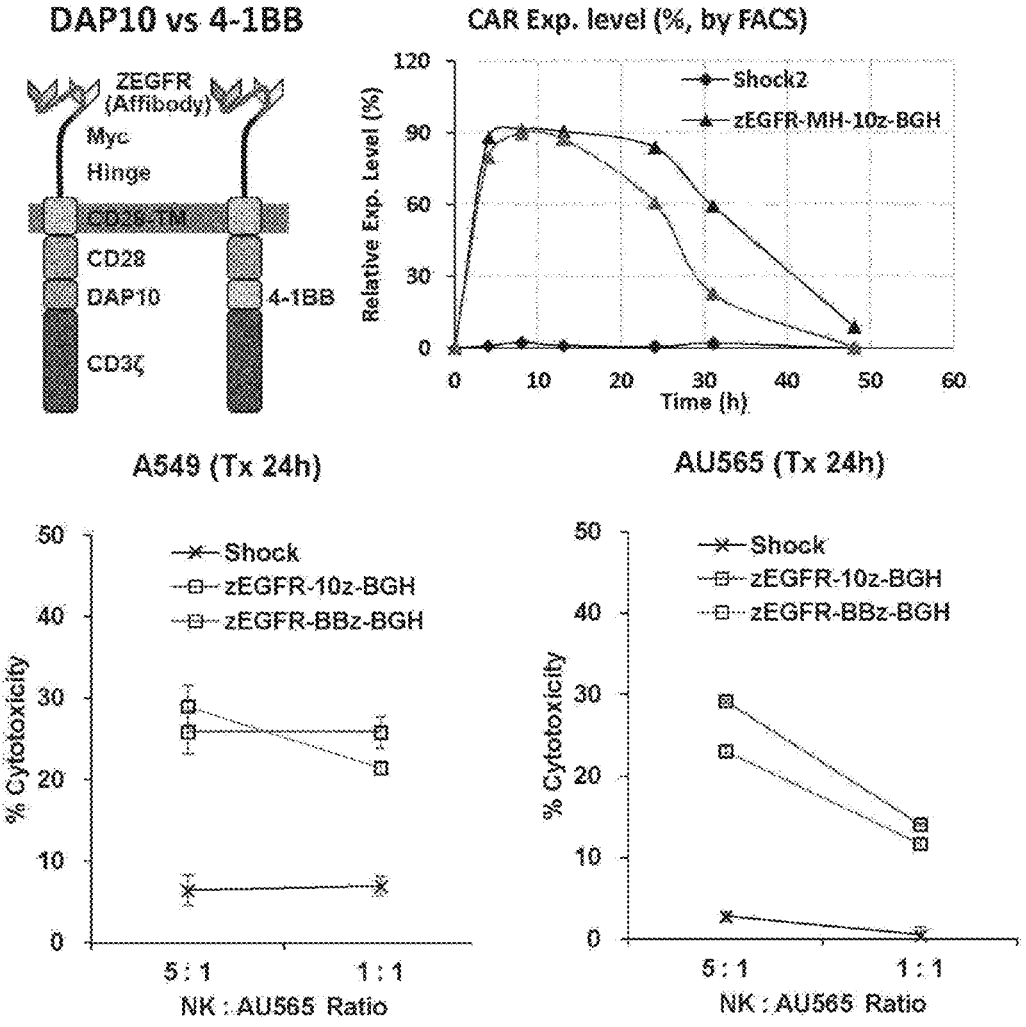
FIG. 9 shows a result of confirming differences in CAR expression levels and cytotoxicity between co-activator DAP10 and 4-1BB in the CAR structure.
Figure 10:
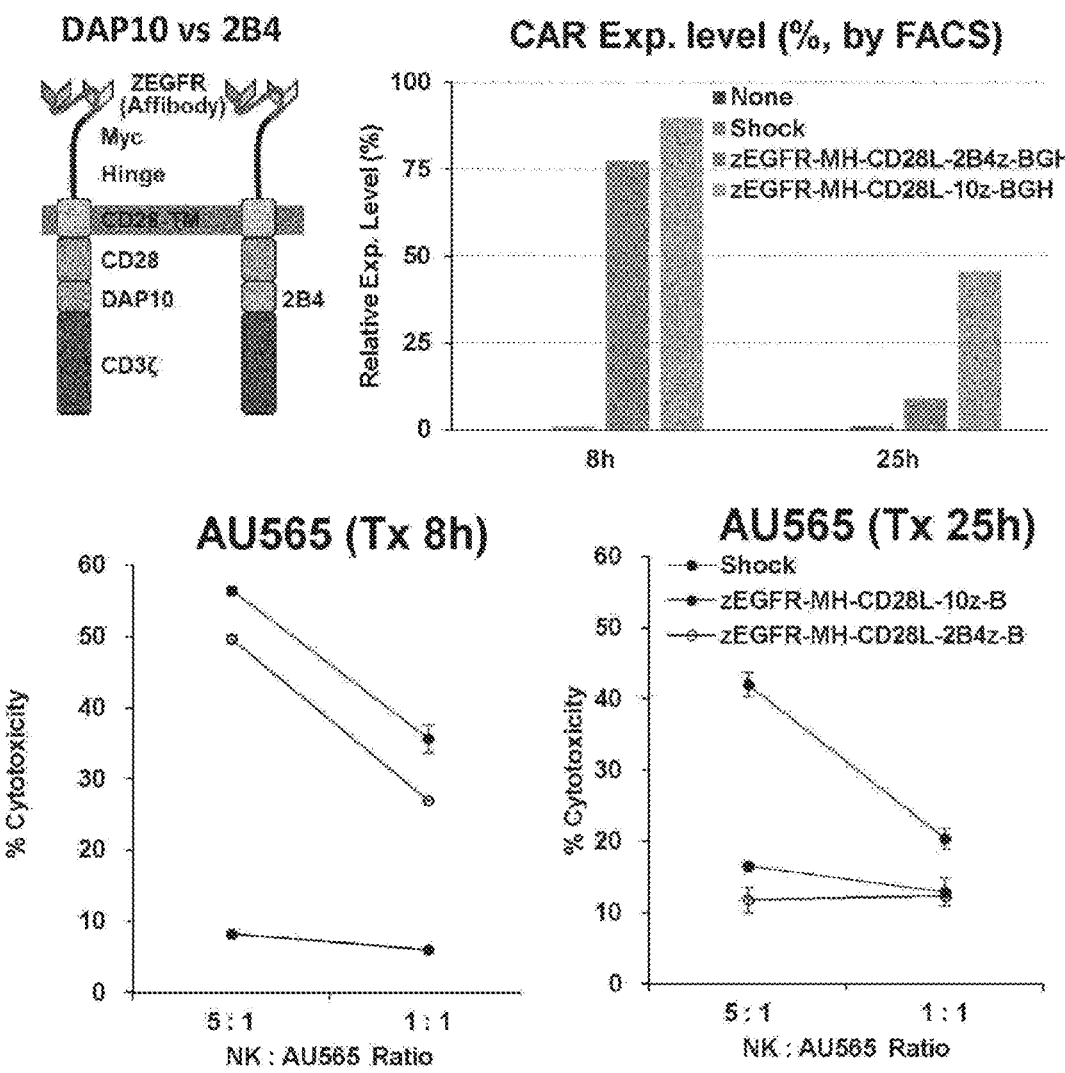
FIG. 10 shows a result of confirming differences in CAR expression levels and cytotoxicity between co-activator DAP10 and 2B4 in the CAR structure.

To evaluate the function and effect of each component constituting the signaling endodomain, ΔEcto-TM-10z, which is free of ectodomain, and ZEGFR-CAR, which has an affibody having anti-EGFR activity as ectodomain, were prepared. For ZEGFR-CAR, ZEGFR-TM vector having ITAM motif and TM motif of CD28 in the pSK vector as background, ZEGFR-TM-10 vector having DAP10 added thereto or ZEGFR-TM-z vector having CD3z added thereto, and ZEGFR-TM-10z vector having both DAP10 and CD3z were constructed (FIG. 6). From here, CAR mRNA were synthesized, and CAR expressions were measured in NK92 cells using FACS (FIG. 7). For ZEGFR-TM-10z having both DAP10 and CD3z, the CAR expression level was similar to ZEGFR-TM-10. Comparison between a third-generation CAR construct having two co-activation motifs such as CD28 and DAP10, and the second-generation CAR construct having only one activation motif, DAP10 results in the finding that the expression level and expression regression ratio of CAR were similar, cytotoxicity was similar at 8 h post transfection of CAR mRNA, and at 25 h post transfection, the second-generation CAR construct showed a higher cytotoxicity (FIG. 8). In addition, when using 4-1BB motif, instead of DAP10 motif, in the third-generation CAR composed of two co-activation domains, ZEGFR-10z using DAP10 motif showed better CAR expression levels and duration than ZEGFR-BBz having 4-1BB motif, and cytotoxicity with respect to lung cancer cell line A549 and breast cancer cell line AU565 were similar, or higher with ZEGFR-10z (FIG. 9). Next, when using 2B4 motif instead of DAP10 motif, ZEGFR-10z using DAP10 motif showed better CAR expression level and duration than ZEGFR-2B4z having 2B4 motif, and cytotoxicity with respect to breast cancer cell line, AU565 cells, performed at 8 h and 25 h post CAR mRNA transfection were also higher with ZEGFR-10z (FIG. 10).

<Example 5> UTR Characterization for Enhancing Structural Stability of mRNA and Target Protein Expression

5-1. Design and Preparation of RNA Constructs

Figure 11A:
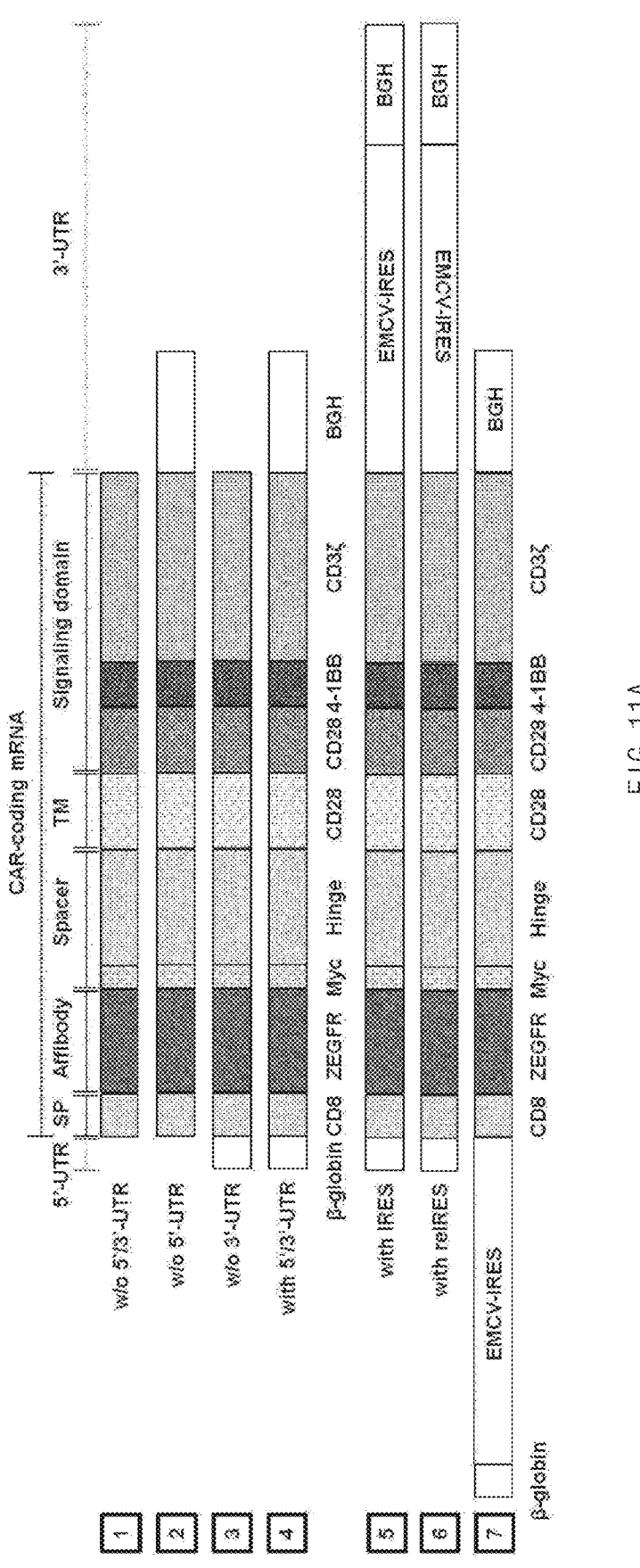
FIG. 11A is a schematic diagram of mRNA constructs designed with or without 5'-β-globin UTR, 3'-BGH, and EMCV-IRES constructs, and by varying the forward/reverse direction or 5'/3' locations of EMCV-IRES.
Figure 11B:
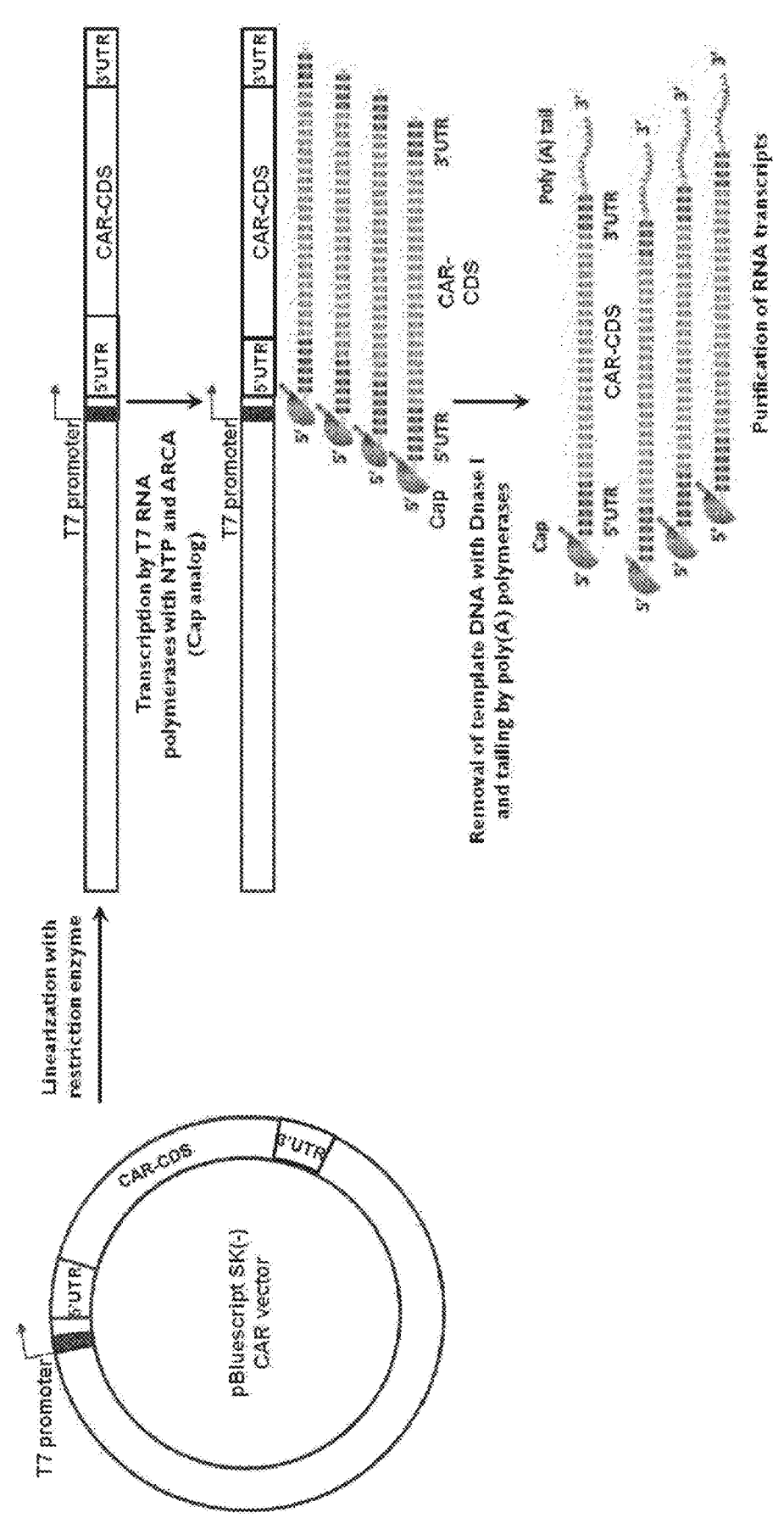
FIG. 11B is a schematic diagram of a preparation process of mRNA constructs.

To enhance the structural stability of mRNA of the target protein and its expressions, mRNA constructs 1-7 with various 5' UTR and 3' UTR modifications were designed (FIG. 11A), and mRNA constructs 1-7 were prepared by obtaining transcriptomes from vectors having T7 promoter region and coding each mRNA construct (FIG. 11B). Table 1 and FIG. 11A show the designed mRNA constructs. DNA sequences complementary to each region contained in the mRNA constructs are shown in Table 2 below.

TABLE 1

| Construct No. | Name | mRNA Size | Rank |
|---|---|---|---|
| 1 | ZE-BBz | 1286 bp | 1 |
| 2 | ZE-BBz-BGH | 1519 bp | 3 |
| 3 | 5U-ZE-BBz | 1345 bp | 2 |
| 4 | 5U-ZE-BBz-BGH | 1578 bp | 4 |
| 5 | 5U-ZE-BBz-IRES-BGH | 2164 bp | 5 |
| 6 | 5U-ZE-BBz-reIRES-BGH | 2164 bp | 5 |
| 7 | 5U-IRES-ZE-BBz-BGH | 2164 bp | 5 |

TABLE 2

| Sequence Number | Gene | Sequence |
|---|---|---|
| 1 | β-globin UTR | ACATTTGCTTCTGACATAGTTGTGTTGACTCACAACCCCAGAAACAGACA TCC |
| 2 | BGH | GCCTCGACTGTGCCTTCTAGTTGCCAGCCATCTGTTGTTTGCCCCTCCCC CGTGCCTTCCTTGACCCTGGAAGGTGCCACTCCCACTGTCCTTTCCTAAT AAAATGAGGAAATTGCATCGCATTGTCTGAGTAGGTGTCATTCTATTCTG GGGGGTGGGGTGGGGCAGGACAGCAAGGGGGAGGATTGGGAAGACAATAG CAGGCATGCTGGGGA |
| 3 | EMCV-IRES | TCCCCCTCTCCCTCCCCCCCCCCCTAACGTTACTGGCCGAAGCCGCTTGG AATAAGGCCGGTGTGCGTTTGTCTATATGTTATTTTCCACCATATTGCCG TCTTTTGGCAATGTGAGGGCCCGGAAACCTGGCCCTGTCTTCTTGACGAG CATTCCTAGGGGTCTTTCCCCTCTCGCCAAAGGAATGCAAGGTCTGTTGA ATGTCGTGAAGGAAGCAGTTCCTCTGGAAGCTTCTTGAAGACAAACAACG TCTGTAGCGACCCTTTGCAGGCAGCGGAACCCCCCACCTGGCGACAGGTG CCTCTGCGGCCAAAAGCCACGTGTATAAGATACACCTGCAAAGGCGGCAC AACCCCAGTGCCACGTTGTGAGTTGGATAGTTGTGGAAAGAGTCAAATGG CTCTCCTCAAGCGTATTCAACAAGGGGCTGAAGGATGCCCAGAAGGTACC CCATTGTATGGGATCTGATCTGGGGCCTCGGTGCACATGCTTTACATGTG TTTAGTCGAGGTTAAAAAACGTCTAGGCCCCCGAACCACGGGACGTGG TTTTCCTTTGAAAAACACGTTGATAATTTG |

The nucleotide sequences of the gene construct encoding the seven mRNA constructs designed as described above were inserted into the pBluescript SK(−) vector (Addgene), and mRNA constructs 1 to 7 were prepared through in vitro transcription as shown in FIG. 11B.

As shown in FIG. 11B, the seven mRNA obtained through in vitro transcription as described above have 5'-Cap and 3'-Poly(A) tails coupled thereto.

5-2. Evaluation on RNA Stability

The seven mRNA obtained in Example 5-1 were transduced into NK92 cells at a voltage of 110V using the Nepa 21 system used in Example 2 to prepare transient CAR-NK cells. For the transient CAR-NK cells prepared as described above, the mRNA level injected into the NK92 cells were monitored over time.

Figure 12:
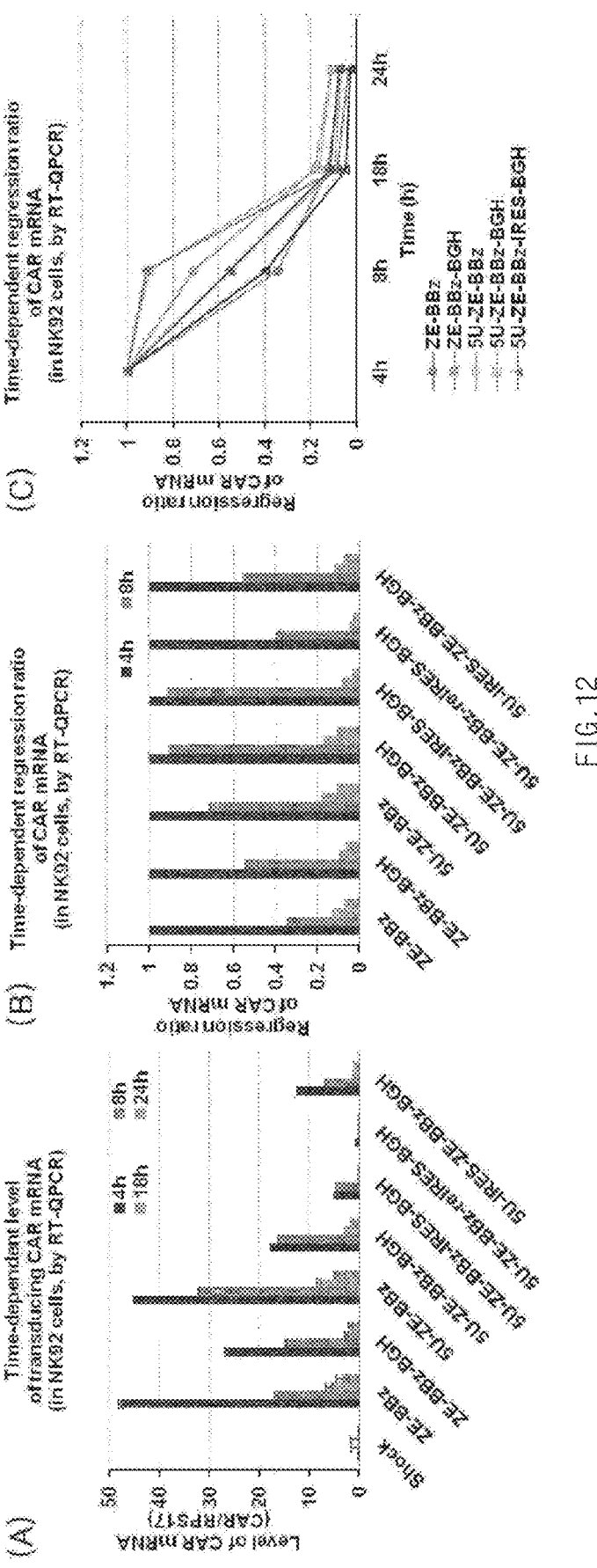
FIG. 12 is a diagram showing the comparison of time-dependent regression ratios of mRNA constructs 1 to 7 introduced into a cell.

To evaluate CAR mRNA stability according to the presence/absence of 5'-β-globin UTR, 3'-BGH, or EMCV-IRES, and 5'/3' location or forward/reverse direction of EMCV-IRES, reduction ratios of the mRNA introduced into cells over time were identified (A of FIG. 12).

As a result, with the amount of mRNA construct present, evaluated at 4 h post transfection, which is in an early stage of transformation, as a reference (1), 5U-ZE-BBz showed an mRNA stability improved by 36.9% than ZE-BBz, and 5U-ZE-BBz-BGH showed an mRNA stability improved by 35.9% than ZE-BBz-BGH, ZE-BBz-BGH showed an mRNA stability improved by 20.2% than ZE-BBz, and 5U-ZE-BBz-BGH showed mRNA stability improved by 19.1% than 5U-ZE-BBz, and U-ZE-BBz-BGH containing both 5'-β-globin and 3'-BGH showed mRNA stability improved by 56.1% than ZE-BBz. Thus, it could be confirmed that the presence of 5'-β-globin and 3'-BGH enhances mRNA stability (B of FIG. 12 and C of FIG. 12).

5-3. Evaluation on Translational Stability

Figure 13:
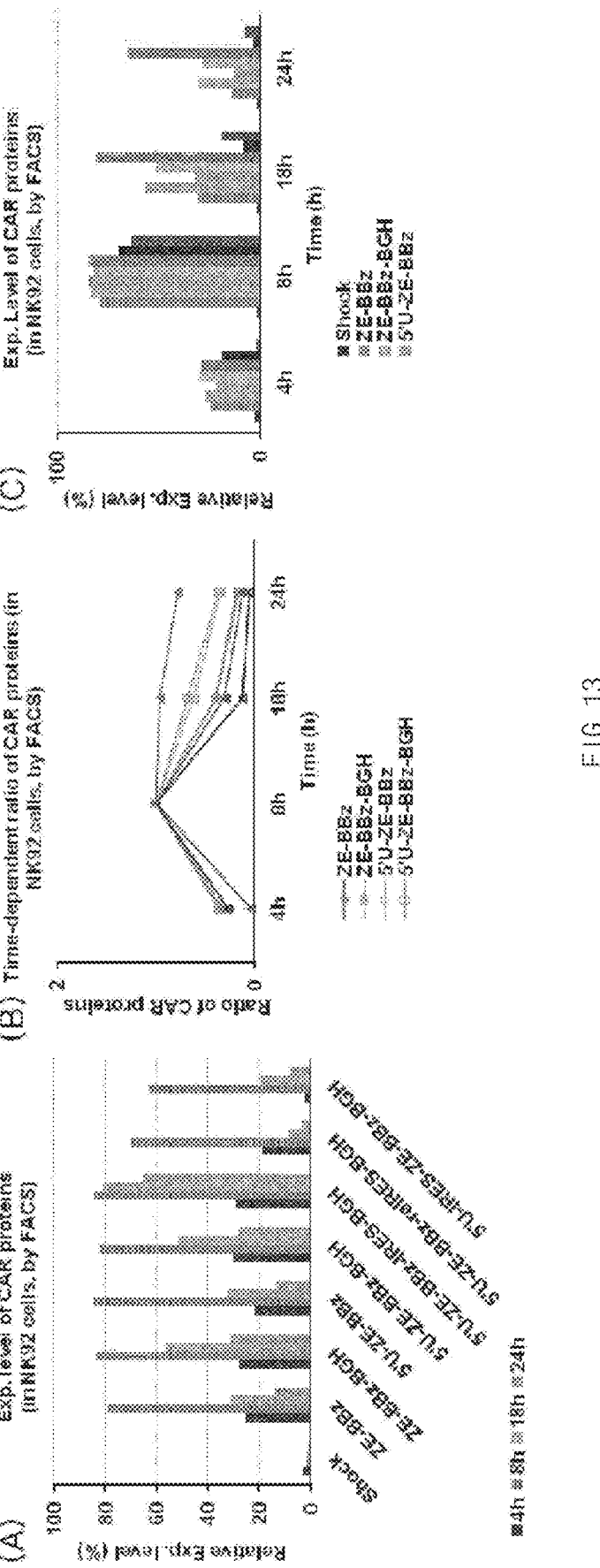
FIG. 13 is diagrams showing comparison and characterization of CAR protein expression levels in transient NK92 cells with mRNA constructs 1 to 7 introduced therein.

Furthermore, for the 7 types of transient CAR-NK cells prepared in Example 5-2, in order to evaluate the translational stability of CAR mRNA over the course of time based on the expression level of the CAR protein expressed at 8 hours after the mRNA was injected into the NK92 cells(1), the degree of decrease in CAR protein expression was checked 4, 8, 18, and 24 hours after transduction was induced. (FIG. 13).

As a result, with the CAR protein expression level at 8 h post transfection induction at which the CAR protein expression is the highest as a reference (1), ZE-BBz-BGH showed a protein expression level improved by 28.4% than ZE-BBz, and 5U-ZE-BBz-BGH showed a protein expression level improved by 24.3% than 5U-ZE-BBz, and 5U-ZE-BBz-IRES-BGH showed a protein expression level improved by 33.3% than 5U-ZE-BBz-BGH. Thus, it could be confirmed that 3'-BGH and 3'-EMCV-IRES contribute to an increase in protein expression levels.

Meanwhile, contrary to the fact that the presence of 3'-EMCV-IRES enhances the expression of protein, the protein expression levels drastically decreased when the looping structure for translation is modified by inserting EMCV-IRES in a reverse direction, and EMCV-IRES is located at 5'.

5-4. Evaluation on Cytolytic Activity

Figure 14A:
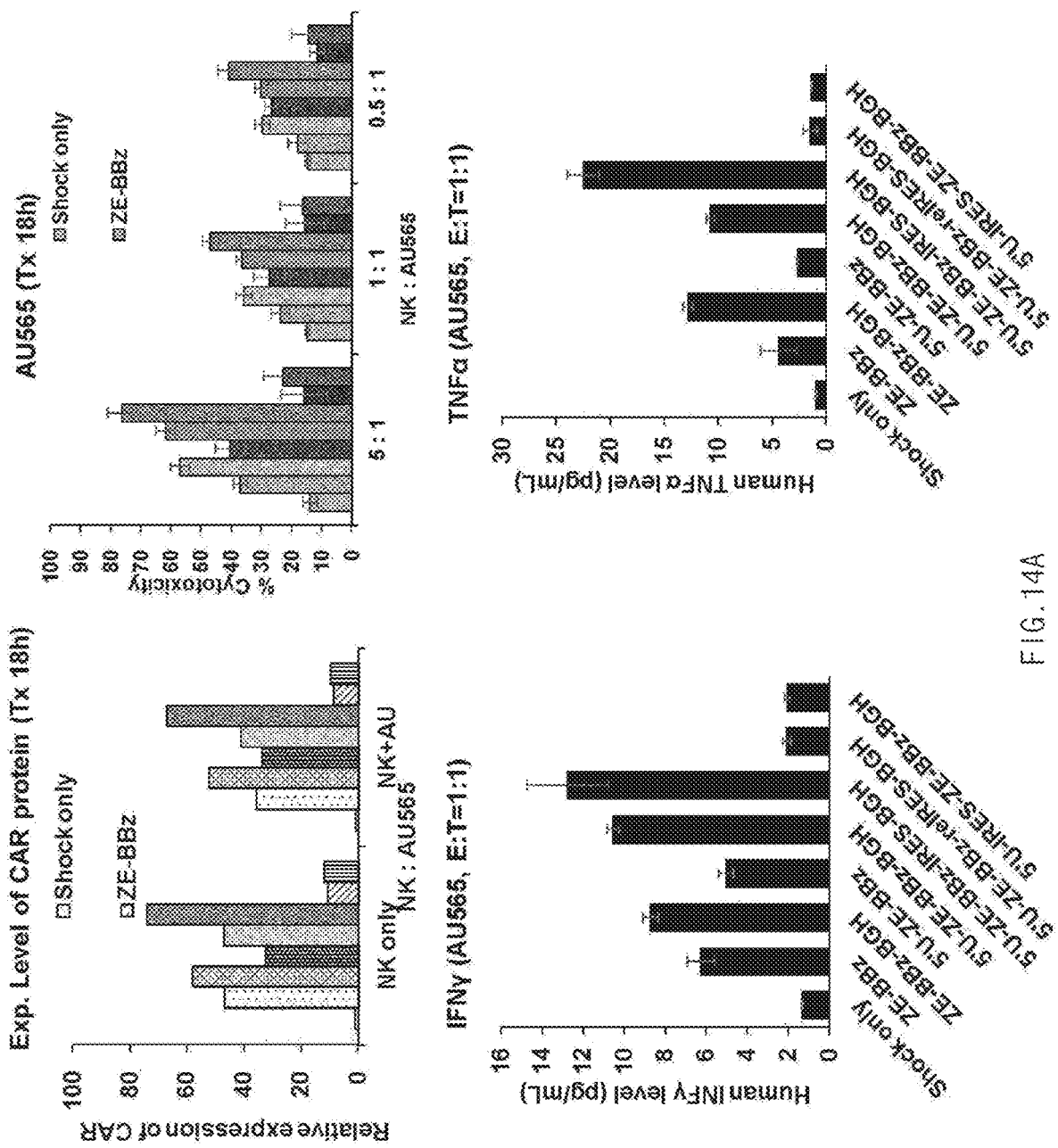
FIGS. 14A and 14B are diagrams showing comparison and characterization of cytotoxicity in a lung cancer cell line and a breast cancer cell line of transient NK92 cells with mRNA constructs 1 to 7 introduced therein.
Figure 14B:
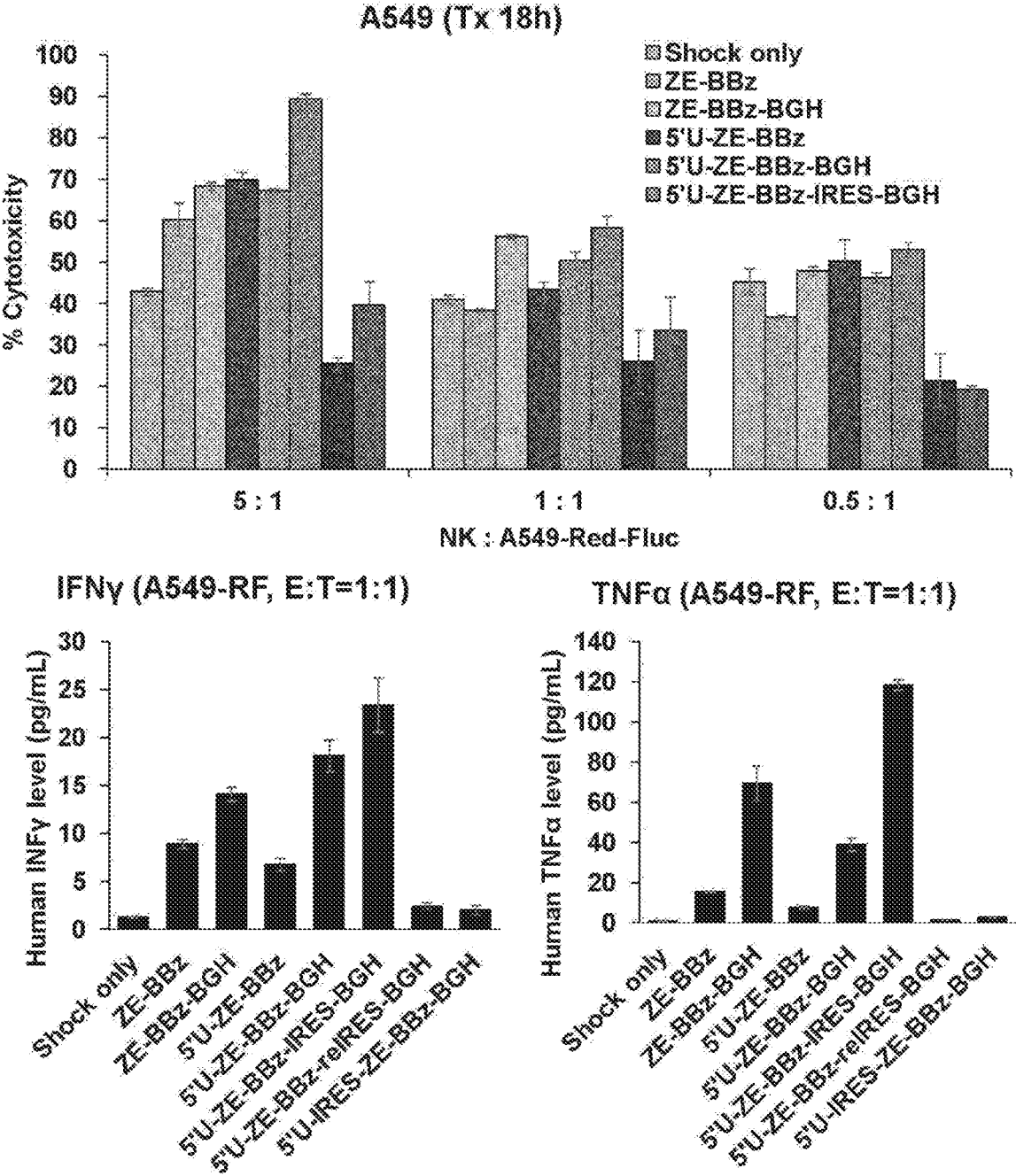

Then, when 18 hours have elapsed after the seven mRNA prepared in Example 5-2 were injected into NK92 cells, in the same manner as in Example 3, the transient CAR-NK cells were treated in breast cancer cell line AU565 and lung cancer cell line A549, respectively, and cytotoxicity to cancer cells was evaluated. (FIG. 14A and FIG. 14B).

As a result, in the transient NK92 cells, cytolytic activity corresponding to the expression level of CAR protein was observed, and a chain of responses, IFNγ and TNFα secretion, also increased in response thereto. The expression level of CAR protein and cytolytic activity were observed to be high in 5U-ZE-BBz-BGH and 5U-ZE-BBz-IRES-BGH, and were the highest in 5U-ZE-BBz-IRES-BGH in particular.

5-5. Comparison Between IRES-BGH and BGH-IRIS

The influence of the sequence of IRES and BGH positioned at 3' UTR was identified.

Figure 15A:
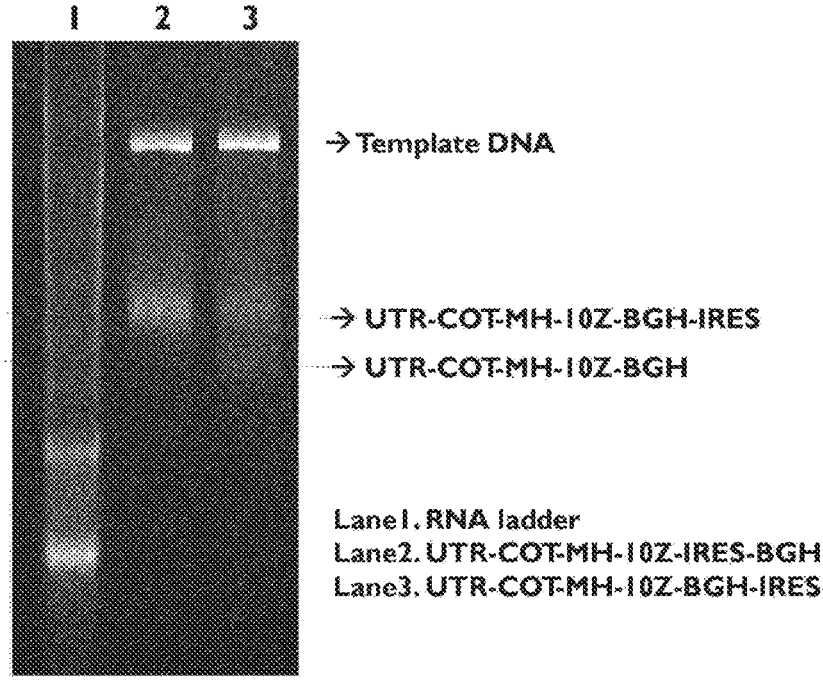
FIG. 15A is electrophoresis for transcriptomes obtained from a vector containing a DNA sequence corresponding or complementary to a base sequence of mRNA with different order of BGH and IRES at 3' terminal.

First, mRNAs were designed as shown in Table 3 below, and the mRNAs were prepared by the method illustrated in FIG. 12 and electrophoresis was performed. As a result, it could be confirmed that for the mRNA with BGH-IRES sequence at 3'UTR, separate transcriptomes without and with IRES were formed in the mRNA, whereas for the mRNA with IRES-BGH, a single mRNA with IRES at 3' UTR was formed. From this result, it could be confirmed that due to a complex two-dimensional structure of IRES, when IRES follows after BGH, separation of IRES from the mRNA occurred (FIG. 15A).

TABLE 3

| Construct No. | Name |
| --- | --- |
| 1 | UTR-COT-MH-10Z-IRES-BGH-PolyA |
| 2 | UTR-COT-MH-10Z-BGH-IRES-PolyA |

Figure 15B:
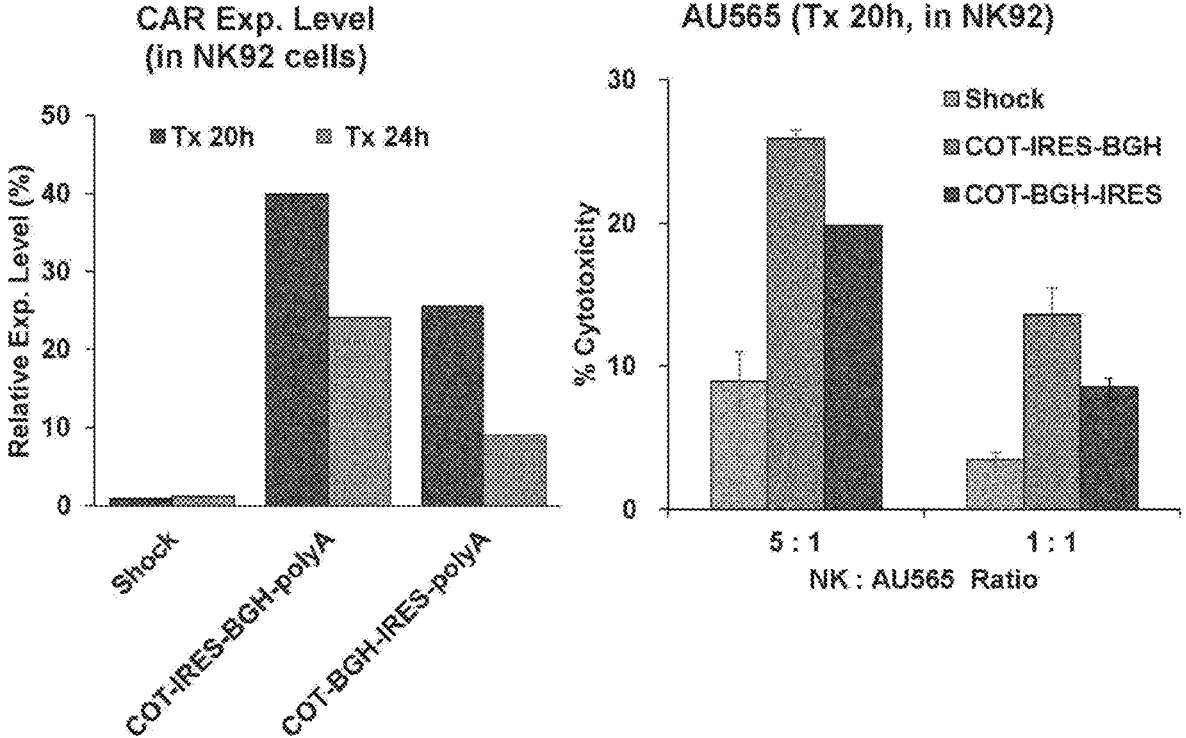
FIG. 15B shows characterizations of the target protein performance and target protein expression efficiency in cells, of mRNA constructs with BGH and IRES in different orders at 3' terminal.

Also, expression levels of CAR protein and cancer cell cytotoxicity were identified by transfecting NK92 cells utilizing the mRNA construct prepared above by the method described in Example 2. As a result, it was confirmed that the mRNA with IRES-BGH sequence expressed CAR protein with high efficiency and showed a higher cancer cell cytotoxicity than that of the mRNA with BGH-IRES sequence (FIG. 15B).

<Example 6> Confirmation of In-Vivo and Ex-Vivo Treatment Results of CAR-NK Cells 6-1. Mouse Intravenous Injection of Target Cells First, $2 \times 10^6$ cells of the lung cancer cell line A549 recombined to express luciferase were intravenously injected into 5 to 6-week-old nude mice. Thereafter, the transient CAR-NK cells prepared by transducing NK92 cells with the four mRNA constructs shown in Table 4 below, were injected intravenously into mice 2 days, 4 days, 7 days and 9 days after the injection of A549 cells for a total of 4 times, as shown in A of FIG. 16.

TABLE 4

| Construct No. | Name |
| --- | --- |
| 1 | 5U-ΔZE-BBz-BGH |
| 2 | 5U-ZE-BBz |
| 3 | 5U-ZE-BBz-BGH |
| 4 | 5U-ZE-BBz-IRES-BGH |

Since the A549 cells express luciferase, when luciferine is injected into the abdominal cavity of a mouse, luminescence occurs in the luciferase-expressing A549 cells throughout the mouse. And A549 cells as described above may be killed by the transient CAR-NK cell cytotoxicity, in which case the luminescence is reduced. The cell death rate of A549 cells was confirmed by measuring the bioluminescence image (BLI) emitted from the cells using IVIS-Spectrum equipment once at weekly intervals.

As a result, as shown in B of FIG. 16, even after 72 days had elapsed, it was confirmed that A549 cells were sufficiently killed when CAR-NK cells expressing the mRNA of constructs No. 2 to No. 4 were treated, compared to construct No. 1, which did not recognize the antigen because there was no ZEGFR region, which is an extracellular domain. Among them, the death rate was the most excellent when CAR-NK cells expressing the mRNA of construct No. 4 having both the 5'-β-globin UTR region and the 3'-IRES-BGH region were treated.

In addition, as shown in C of FIG. 16, ex-vivo BLI was measured by extracting the lung tissue of the mouse at the lapse of 102 days. As confirmed in-vivo, A549 cells were sufficiently killed when CAR-NK cells expressing the mRNA of constructs No. 2 to No. 4 were treated, and was particularly excellent when treated with CAR-NK cells of constructs No. 3 and No. 4.

6-2. Direct Injection of Target Cells into the Mouse Lung $2 \times 10^6$ A549 cells expressing luciferase were directly injected into the lungs of nude mice aged 5 to 6 weeks. After that, as shown in A of FIG. 17, transient CAR-NK cells expressing the CARs of mRNA constructs No. 1, No. 3 and No. 4 of Table 4 over a total of 4 times on Day 7, Day 9, Day 12, and Day 15 days were injected through a mouse vein. By measuring BLI by the method described in 6-1 above, the cell death rate of A549 cells was confirmed.

As a result, as shown in B of FIG. 17, even when A549 cells were directly injected into the mouse lung, compared to construct 1, which did not recognize the antigen because there was no extracellular region, it was confirmed that the number of A549 cells injected into the lung was further reduced when CAR-NK cells expressing the mRNA of constructs No. 3 and No. 4 having 5'-β-globin UTR region and 3'-IRES-BGH region were treated. Among them, the highest A549 cell death rate was exhibited when CAR-NK cells of construct No. 4 including the IRES region were treated.

When the CAR-NK cells expressing the constructs No. 3 and No. 4 were treated, it was confirmed that the mice survived longer than when the CAR-NK cells of the construct No. 1 were treated, as can be seen in the survival curve of C of FIG. 17.

<Example 7> Confirmation of the Stability of the mRNA of the Spike Protein

In order to confirm that the effect of improving stability through the mRNA construct of the present invention is not limited to CAR, the construct of the present invention was applied to the mRNA of spike protein (Sprotein) as a target protein, an active ingredient of BNT162b2, a COVID19 mRNA vaccine of Pfizer-BioNTech. Specifically, as shown in Table 5 below, a 5'-β-globin UTR region was added upstream of the nucleotide sequence encoding the Sprotein, and a construct including an IRES-BGH region was designed downstream (construct No. 11).

TABLE 5

| Construct No. | Name |
| --- | --- |
| 11 | 5U-Sprotein-IRES-BGH |

After that, the mRNA construct designed as described above was in-vitro transcribed in the same manner as in Example 5 to obtain mRNA, which was transduced into HEK-293T cells, and the mRNA expression stability and innate immunogenicity of spike protein (Sprotein) were compared with the Pfizer-BioNtech's COVID19 mRNA vaccine BNT162b2.

First, the expression level of Sprotein was confirmed by western blot. As a result, compared to BNT162b2 (Reference), when the mRNA construct of the present invention was transduced (structure No. 11), the expression level of Sprotein was higher. Specifically, in both constructs, the Sprotein expression level was the highest at 10 hours after transduction, but when the construct No. 11 was transduced, the Sprotein expression level was higher than that in the case of transducing BNT162b2 at 10 hours. After 24 hours, almost no protein was identified in the case of BNT162b2, but it was confirmed that the protein was stably maintained in the case of construct No. 11. In the case of construct No. 11, almost no Sprotein expression was identified at when 48 hours had elapsed.

In particular, as shown in A of FIG. 18, when the construct No. 11 of the present invention was used, it was confirmed that the degree of activation of IRF3, which induces an immune response in host cells in response to external RNA, was also lowered. From the above results, it was confirmed that the target protein can be expressed in a more stable and high amount in a subject when the mRNA construct of the present invention is used.

In addition, in the case of the Sprotein expressed according to the construct of the present invention, it was confirmed through the expression levels of IFNα, IFNβ and ISG15 genes whether there was any change in the activity inducing innate immunogenicity. As a result, as shown in B of FIG. 18, when the mRNA construct of construct No. 11 of the present invention was transduced, the expression levels of IFNα, IFNβ and ISG15 genes were similar when compared to the case where BNT162b2 was injected. Therefore, it was confirmed that there was no significant difference in induction of innate immunogenicity.

From the above results, it was confirmed that by applying the mRNA construct of the present invention, a target protein other than a CAR construct could be stably expressed.

The invention claimed is:

1. An mRNA construct, comprising: (a) a target protein or peptide coding region; and (b) an IRES region downstream of the target protein or peptide coding region, wherein the mRNA construct further comprises a 5'-β-globin UTR region upstream of the target protein or peptide coding region, the mRNA construct further comprises a BGH 3'-UTR region downstream of the target protein or peptide coding region, and the IRES region is included between the target protein or peptide coding region and the BGH 3'-UTR region.

2. The mRNA construct of claim 1, wherein the IRES region comprises a sequence of SEQ ID NO: 3.

3. The mRNA construct of claim 1, wherein the 5'-β-globin UTR region comprises a sequence of SEQ ID NO: 1.

4. The mRNA construct of claim 1, wherein the BGH 3'-UTR region comprises a sequence of SEQ ID NO: 2.

5. The mRNA construct of claim 1, wherein the mRNA construct further comprises a 5'-Cap and a 3'-Poly A tail region.

6. The mRNA construct of claim 1, wherein the target protein or peptide is a chimeric antigen receptor (CAR).

7. A recombinant vector, comprising a DNA base sequence corresponding or complementary to a base sequence of the mRNA construct of claim 1.

8. A transformant, wherein the mRNA construct of claim 1 is introduced into a host cell.

9. The transformant of claim 8, wherein the host cell is an immune cell.

10. A cell therapy composition comprising the transformant of claim 8.

11. The cell therapy composition of claim 10, wherein the cell therapy composition is an anti-cancer drug.

12. The cell therapy composition of claim 11, wherein the cancer is a solid cancer.

* * * * *

SEQUENCE LISTING

```
<160> NUMBER OF SEQ ID NOS: 3

<210> SEQ ID NO 1
<211> LENGTH: 53
<212> TYPE: DNA
<213> ORGANISM: Artificial Sequence
<220> FEATURE:
<223> OTHER INFORMATION: Synthesized

<400> SEQUENCE: 1
acatttgctt ctgacatagt tgtgttgact cacaacccca gaaacagaca tcc          53

<210> SEQ ID NO 2
<211> LENGTH: 215
<212> TYPE: DNA
<213> ORGANISM: Artificial Sequence
<220> FEATURE:
<223> OTHER INFORMATION: Synthesized

<400> SEQUENCE: 2
gcctcgactg tgccttctag ttgccagcca tctgttgttt gcccctcccc cgtgccttcc      60
ttgaccctgg aaggtgccac tcccactgtc ctttcctaat aaaatgagga aattgcatcg     120
cattgtctga gtaggtgtca ttctattctg gggggtgggg tggggcagga cagcaagggg     180
gaggattggg aagacaatag caggcatgct gggga                                215

<210> SEQ ID NO 3
<211> LENGTH: 580
<212> TYPE: DNA
<213> ORGANISM: Artificial Sequence
<220> FEATURE:
<223> OTHER INFORMATION: Synthesized
```

-continued

```
<400> SEQUENCE: 3 tcccctctc cctcccccc cccctaacgt tactggccga agccgcttgg aataaggccg        60
gtgtgcgttt gtctatatgt tattttccac catattgccg tcttttggca atgtgagggc       120
ccggaaacct ggccctgtct tcttgacgag cattcctagg ggtctttccc ctctcgccaa       180
aggaatgcaa ggtctgttga atgtcgtgaa ggaagcagtt cctctggaag cttcttgaag       240
acaaacaacg tctgtagcga ccctttgcag gcagcggaac cccccacctg gcgacaggtg       300
cctctgcggc caaaagccac gtgtataaga tacacctgca aaggcggcac aaccccagtg       360
ccacgttgtg agttggatag ttgtggaaag agtcaaatgg ctctcctcaa gcgtattcaa       420
caaggggctg aaggatgccc agaaggtacc ccattgtatg ggatctgatc tggggcctcg       480
gtgcacatgc tttacatgtg tttagtcgag gttaaaaaac gtctaggccc cccgaaccac       540
ggggacgtgg ttttcctttg aaaaacacgt tgataatttg                             580
```